(12) United States Patent
Burn et al.

(10) Patent No.: US 11,345,717 B2
(45) Date of Patent: May 31, 2022

(54) DETECTION METHOD

(71) Applicant: THE UNIVERSITY OF QUEENSLAND, St. Lucia (AU)

(72) Inventors: Paul Leslie Burn, Kenmore (AU); Paul Edward Shaw, Chelmer (AU); Shengqiang Fan, Chapel Hill (AU)

(73) Assignee: THE UNIVERSITY OF QUEENSLAND, St Lucia (AU)

( * ) Notice: Subject to any disclaimer, the term of this patent is extended or adjusted under 35 U.S.C. 154(b) by 0 days.

(21) Appl. No.: 16/636,132

(22) PCT Filed: Aug. 2, 2018

(86) PCT No.: PCT/AU2018/050805
§ 371 (c)(1),
(2) Date: Feb. 3, 2020

(87) PCT Pub. No.: WO2019/023753
PCT Pub. Date: Feb. 7, 2019

(65) Prior Publication Data
US 2020/0172561 A1 Jun. 4, 2020

(30) Foreign Application Priority Data
Aug. 3, 2017 (AU) .............................. 2017903079

(51) Int. Cl.
*G01N 21/77* (2006.01)
*G01N 33/22* (2006.01)
*G01N 31/22* (2006.01)
*C07F 5/02* (2006.01)

(52) U.S. Cl.
CPC ............. *C07F 5/027* (2013.01); *G01N 21/77* (2013.01); *G01N 33/227* (2013.01); *G01N 31/228* (2013.01); *G01N 2021/7769* (2013.01); *G01N 2021/7786* (2013.01); *Y10T 436/206664* (2015.01)

(58) Field of Classification Search
CPC . C07F 5/025; C07F 5/027; G01N 2021/7769; G01N 2021/7786; G01N 21/77; G01N 31/228; G01N 33/0057; G01N 33/22; G01N 33/227; Y10T 436/141111; Y10T 436/142222; Y10T 436/203332; Y10T 436/206664; Y10T 436/25875
USPC ... 436/92, 93, 131, 135, 164, 167, 172, 181; 422/82.05, 82.08, 83, 88
See application file for complete search history.

(56) References Cited

U.S. PATENT DOCUMENTS

| | | | |
|---|---|---|---|
| 8,137,990 B2 * | 3/2012 | Akhavan-Tafti | G01N 33/533 436/546 |
| 8,999,722 B2 * | 4/2015 | Swager | G01N 21/643 436/98 |
| 9,018,377 B2 * | 4/2015 | He | C07D 221/14 546/100 |
| 9,429,522 B2 * | 8/2016 | Swager | G01N 33/0057 |
| 10,151,700 B2 * | 12/2018 | Burn | G01N 33/0057 |
| 2011/0130306 A1 * | 6/2011 | Chang | C12Q 1/28 506/15 |
| 2012/0149601 A1 * | 6/2012 | Knapp | G01N 21/643 506/21 |
| 2014/0193923 A1 | 7/2014 | Zang et al. | |
| 2014/0248218 A1 * | 9/2014 | Daniel | A61K 49/0039 424/9.6 |

FOREIGN PATENT DOCUMENTS

| | | |
|---|---|---|
| CN | 106967102 | 7/2017 |
| WO | 2009/152102 A2 | 12/2009 |
| WO | 2014/085858 | 6/2014 |

OTHER PUBLICATIONS

Fan et al. RSC Advances, vol. 9, pp. 7032-7042. Mar. 1, 2019.*
Xu et al. Biosensors and Bioelectronics, vol. 56, pp. 58-63, Jan. 9, 2014.*
Fu, Yanyan, et al., "A BODIPY dye as a reactive chromophoric/fluorogenic probe for selective and quick detection of vapors of secondary amines", ChemComm, 2013, vol. 49, pp. 11266-11268.
Fu, Yanyan, et al., "Schiff Base Substituent-Triggered Efficient Deboration Reaction and Its Application in Highly Sensitive Hydrogen Peroxide Vapor Detection", Analytical Chemistry, 2016, vol. 88, pp. 5507-5512.
Link, J. E., et al., "Applications of a Boronate Ester Coordination Polymer for Sensing and Storing of Benzene", Polymer Preprints, 2010, vol. 51, No. 2, pp. 461-462.
International Preliminary Report on Patentability dated Feb. 13, 2020, issued in International Application No. PCT/AU2018/050805, 9 pages.
International Search Report for PCT/AU2018/050805 dated Sep. 10, 2018, 4 pages.
Du, Lupei, et al., "Rational Design of a Fluorescent Hydrogen Peroxide Probe Based on the Umbelliferone Fluorophore", Tetrahedron Letters, vol. 49, No. 19, May 5, 2008, pp. 3045-3048.
Shäferling, Michael, et al., "Luminescent probes for detection and imaging of hydrogen peroxide", Microchimica Acta, vol. 174, No. 1-2, Apr. 26, 2011, pp. 1-18.
Communication enclosing the Extended European Search Report dated Mar. 15, 2021, issued in European Application No. 18842150.7, 9 pages.

* cited by examiner

*Primary Examiner* — Maureen Wallenhorst

(74) *Attorney, Agent, or Firm* — Nixon & Vanderhye P.C.

(57) ABSTRACT

An optical sensing element for use in the detection of hydrogen peroxide includes a sensing compound provided as a coating on a substrate. The sensing compound, on exposure to hydrogen peroxide, forms a luminescent reporter compound when excited with stimulating radiation at a predetermined wavelength that the sensing compound does not absorb.

9 Claims, 14 Drawing Sheets

DETECTION METHOD

This application is the U.S. national phase of International Application No. PCT/AU2018/050805 filed Aug. 2, 2018 which designated the U.S. and claims priority to AU Patent Application No. 2017903079 filed Aug. 3, 2017, the entire contents of each of which are hereby incorporated by reference.

FIELD OF THE INVENTION

The present invention relates to optical sensing elements for the detection of analytes, in particular hydrogen peroxide and organic peroxides that can be decomposed to yield hydrogen peroxide.

BACKGROUND TO THE INVENTION

Organic peroxides, such as triacetone triperoxide (TATP), diacetone diperoxide (DADP) and hexamethylene triperoxide diamine (HMTD), are unstable but can be manufactured by relatively simple reactions, for example, TATP can be synthesised using commercially available hydrogen peroxide ($H_2O_2$) and acetone. These organic peroxides are now being used as explosives and they are powerful and destructive like nitro-based explosives. Use by terrorists of organic peroxide explosives is becoming common. Detection of organic peroxide type explosives is therefore very important. In applications such as airport security screening, the detection technique used should ideally be non-destructive for the item screened.

Various approaches for detection of organic peroxide explosives have been investigated. Traditional detection methods involving electrochemistry, chromatography, mass spectrometry and biochemistry have been developed. However, these methods are conducted in solution and/or require bulky and complex equipment. They are therefore not all that practical to implement in contexts where rapid, high volume and cost-effective testing is required, such as at airports.

Vapour phase detection of nitro-based explosives and taggants using fluorescent probes has been found to be effective. The nitro-based explosives and taggants cause a decrease in the luminescence of the fluorescence probes and it is this decrease in luminescence that indicates that such analytes are present. Such probes may provide excellent sensitivity and quick response. The probes also tend to be highly portable. However, this approach is not straightforward to implement for organic peroxide explosives because they are not typical fluorescence quenching agents. Unlike the nitro-based explosives, the peroxide explosive compounds do not have nitro groups and aromatic rings that give rise to an electron affinity that is sufficient to quench the luminescence of the fluorescent probes.

US 2014/0193923A1 describes a sensor for detecting hydrogen peroxide comprising a porous hydrophilic material modified with particular π conjugated molecules. The π conjugated molecules (also referred to as "sensor molecules") are said to react with hydrogen peroxide to provide an optical change. It is noted that the sensor molecules are non-fluorescent or weakly fluorescent in the pristine state which means a "zero" background. However, on reaction with hydrogen peroxide the sensor molecules form an intramolecular charge transfer state which is said to increase the molar extinction coefficient in the visible region enabling colorimetric sensing, and a turn-on fluorescent response enabling fluorescence sensing. It is evident that what is meant by turn-on fluorescent response in this context is that in the pristine state the sensor molecule absorbs electromagnetic radiation but there is no related emission from the molecule, i.e. there is no fluorescence. However, when the sensor molecule is exposed to hydrogen peroxide, the reacted molecule will also absorb and there is a related emission, i.e. the molecule when reacted becomes fluorescent. This is a critical property of the sensor molecules to be used.

In US 2014/0193923A1 the nature of the substrate upon which the sensor molecules are provided is also important. The substrate must be hydrophilic to enable sensor molecules to be bound to it. The substrate must also be porous. This characteristic is important because it is said to provide a large surface area and porosity that is conducive to sampling and detection of vapor phase samples. It is also implied that the use of solid thin films of the sensor molecule would not be useful because the detection limit would be poor due to surface area and air sampling effects.

The porous materials used will be non-transparent and scattering to exciting radiation because of internal reflections taking place within the material. This is dealt with in US 2014/0193923A1 by taking measurements in reflection mode.

US 2014/0193923A1 therefore has certain operating limitations with respect to the optical characteristics of the sensor molecules used, the substrate upon which the sensor molecules are to be provided for vapor phase detection and the detection methodology that can be employed.

The present invention seeks to provide detection technology that may be applied to detect organic peroxide explosives, that is non-destructive to the object being screened, that provides suitably high sensitivity and response time, and that may be implemented using compact and portable devices. In embodiments the present invention also seeks to avoid various limitations associated with known approaches described.

SUMMARY OF THE INVENTION

In an embodiment the present invention provides an optical sensing element for vapour phase detection of hydrogen peroxide, the optical sensing element comprising a sensing compound provided on a substrate, wherein the sensing compound is a compound that on exposure to hydrogen peroxide forms a luminescent reporter compound that can be excited with stimulating radiation at a predetermined wavelength that the sensing compound does not absorb.

The present invention also provides a method for vapor phase detection of hydrogen peroxide in a sample, which method comprises: (a) irradiating an optical sensing element in accordance with the present invention at the predetermined wavelength; (b) contacting the sample with the optical sensing element; (c) measuring the luminescence of the optical sensing element after contacting with the sample; and (d) determining whether hydrogen peroxide is present in the sample based on the measurement obtained in step (c). The optical sensing element is irradiated continuously or with pulses at least during steps (b) and (c).

The present invention also provides a sensing device in which the optical sensing element would be used. Accordingly, in this embodiment the present invention provides a sensing device for vapour phase detection of hydrogen peroxide in a sample, the sensing device comprising:

an optical sensing element in accordance with the present invention;

an irradiation source for irradiating the optical sensing element with stimulating radiation at the predetermined wavelength;

a detector for measuring luminescence of the optical sensing element;

means for relating to an operator the luminescence measured by the detector; and means for delivering the sample for contacting with the optical sensing element.

The present invention may be applied for detection of an organic peroxide that can be decomposed to yield hydrogen peroxide. Accordingly, in another embodiment the present invention provides a method of detecting an organic peroxide in a sample, the method comprising: (a) processing the sample to cause organic peroxide in the sample to decompose to yield vapour of hydrogen peroxide to produce a conditioned sample; (b) irradiating an optical sensing element in accordance with the present invention at the predetermined wavelength; (c) contacting the conditioned sample with the optical sensing element; (d) measuring the luminescence of the optical sensing element after contacting with the conditioned sample; (e) determining whether hydrogen peroxide is present in the conditioned sample based on the measurement obtained in (d); and (e) using a determination that hydrogen peroxide is present in step (d) as indication that the organic peroxide is present in the sample.

In another embodiment the present invention provides a sensing device for detecting organic peroxide in a sample, the sensing device comprising: (a) means for decomposing organic peroxide in the sample to hydrogen peroxide to produce a conditioned sample; (b) an optical sensing element in accordance with the present invention; (c) an irradiation source for irradiating the optical sensing element with stimulating radiation at the predetermined wavelength; (d) a detector for measuring luminescence of the optical sensing element; (e) a means for relating to an operator luminescence measured by the detector; and (f) a means for delivering the conditioned sample for contacting with the optical sensing element.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

BRIEF DISCUSSION OF DRAWINGS

Embodiments of the present invention are illustrated with reference to the accompanying non-limiting drawings in which:

FIG. 1a is a graph showing UV-vis absorption and photoluminescence (PL) spectra of film comprising SQF0724. The film was prepared by drop casting from a mixture of SQF0724 and n-Bu$_4$NOH (molar ration 1:6) in ethanol. For the PL spectra, the excitation wavelength was 388 nm. [TATP] represents the conditioned sample from TATP generated using Amberlyst-15 as catalyst.

FIG. 1b is a graph showing UV-vis absorption and PL spectra of a film comprising SQF07114. The film was prepared by drop casting from a mixture of SQF07114 and n-Bu$_4$NOH (molar ratio 1:6) in ethanol. For the PL spectra, the excitation wavelength was 365 nm. [TATP] represents the conditioned sample from TATP generated using Amberlyst-15 as catalyst.

FIG. 1c is a graph showing UV-vis absorption and PL spectra of a film comprising SQF0784. The film was prepared by drop casting from a mixture of SQF0784 and n-Bu$_4$NOH (molar ration 1:6) in ethanol. For the PL spectra, the excitation wavelength was 390 nm. [TATP] represents the conditioned sample from TATP generated using Amberlyst-15 as catalyst.

FIG. 1d is a graph showing UV-vis absorption and PL spectra of a film comprising a comparative compound, SQF1044. The film was prepared by drop casting from a mixture of SQF1044 and n-Bu$_4$NOH (molar ratio 1:6) in ethanol. For the PL spectra, the excitation wavelength was 340 nm. [TATP] represents the conditioned sample from TATP generated using Amberlyst-15 as catalyst.

FIG. 2 is a graph showing the PL response of capillary coated internally with a film comprising SQF0724 versus time with vapours of each analyte applied independently. (a) Naphthalene, (b) ethanol, (c) 2,3-dimethyl-2,3-dinitrobutane (DMNB), (d) 2,4-dinitrotoluene (DNT), (e) Listerine, (f) antiperspirant, (g) hairspray, (h) shower gel, (i) perfume, (j) sunscreen, and (k) Conditioned sample from TATP generated using Amberlyst-15 as catalyst.

Figure 5:
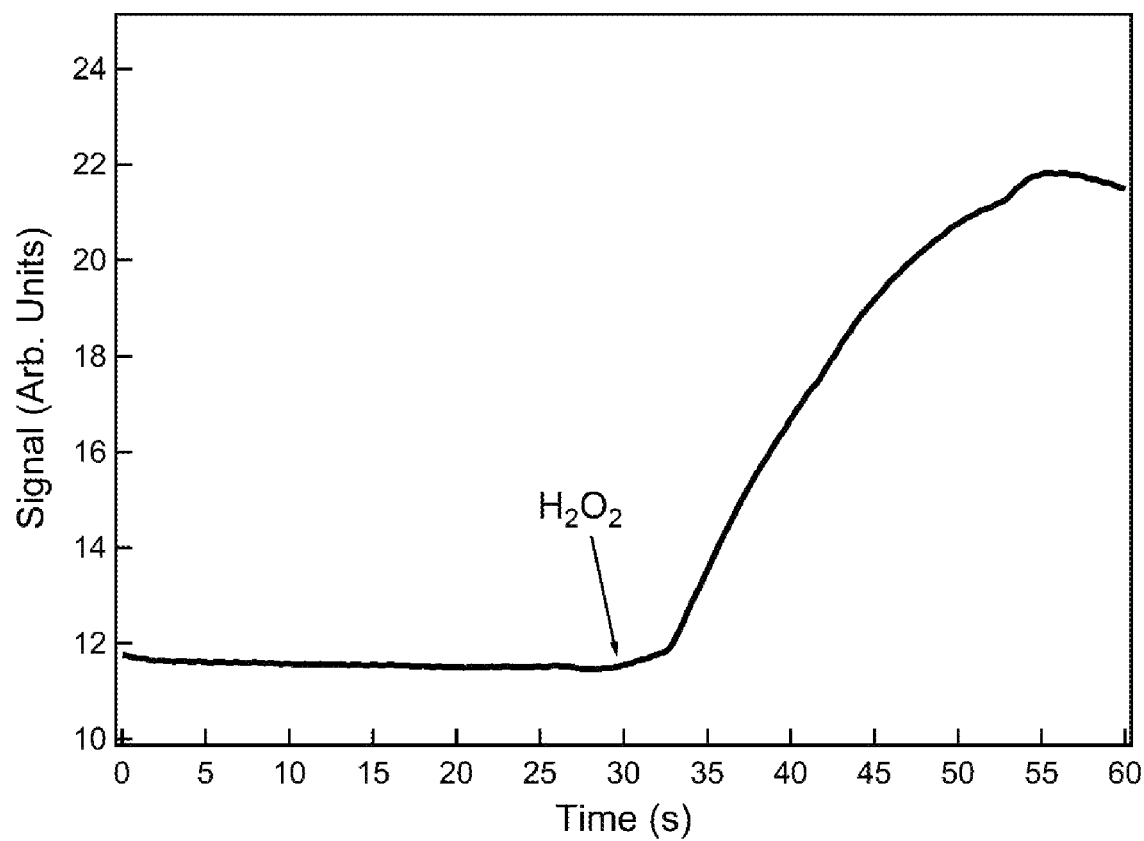

FIG. 5 is a graph showing the PL response of capillary coated internally with a film comprising SQF07114 upon exposing to hydrogen peroxide vapour. The detector is approaching to, but not directly extending to, the headspace of 30% H$_2$O$_2$ aqueous solution. Base: n-Bu$_4$NOH (6 eq).

Figure 6:
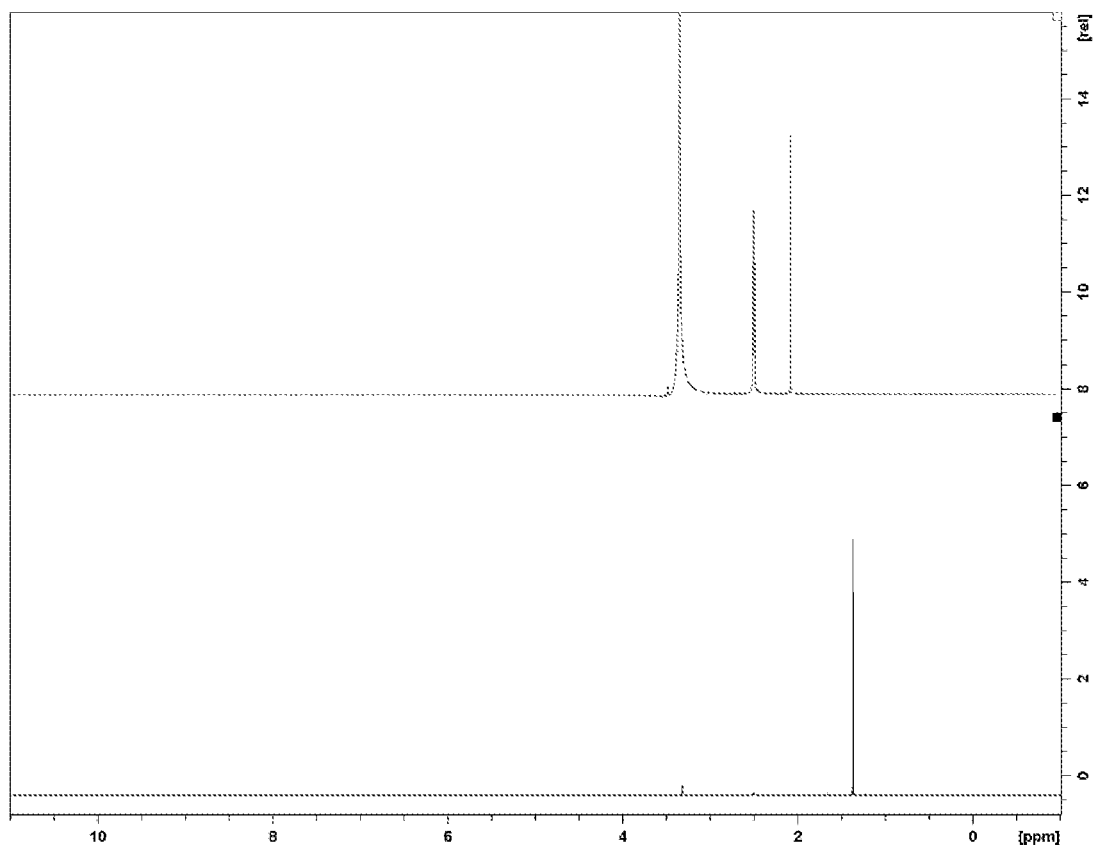

FIG. 6 illustrates $^1$H NMR spectra of TATP (bottom spectrum) and decomposed products of TATP vapour (top spectrum). Spectra were acquired in deuterated dimethyl sulfoxide (DMSO-d6).

Figure 7A:
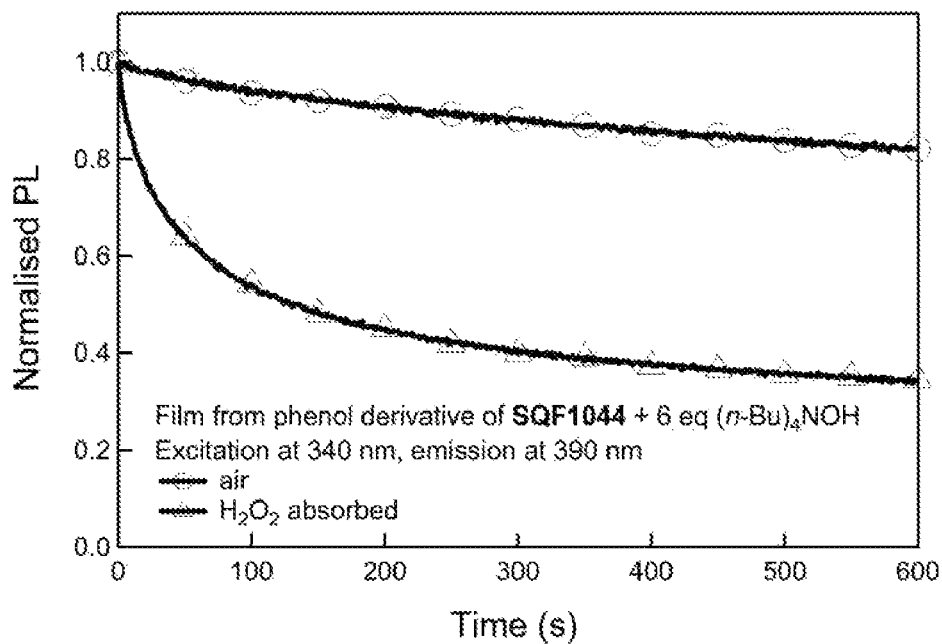
Figure 7B:
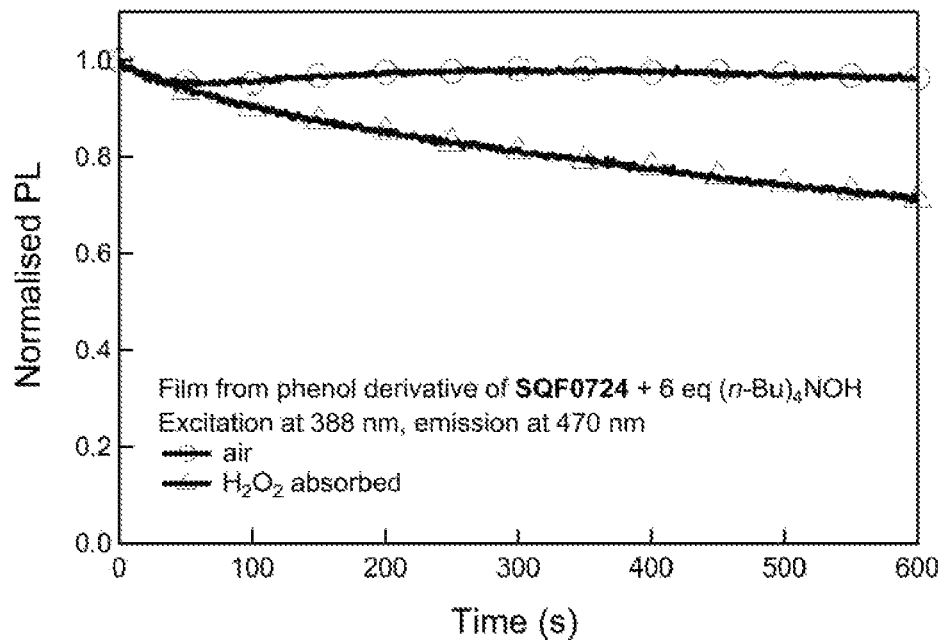

FIG. 7 illustrates the photostability of the phenoxides corresponding to SQF0724 (FIG. 7b) and comparative example SQF1044 (FIG. 7a) in the presence H$_2$O$_2$ or oxygen. The results show that the compound with the electron withdrawing group attached (SQF0724) has the greater photostability. To test the effect of $H_2O_2$, the films were exposed to 221 ppm $H_2O_2$ vapour for 30 seconds before measuring the photostability.

Figure 8:
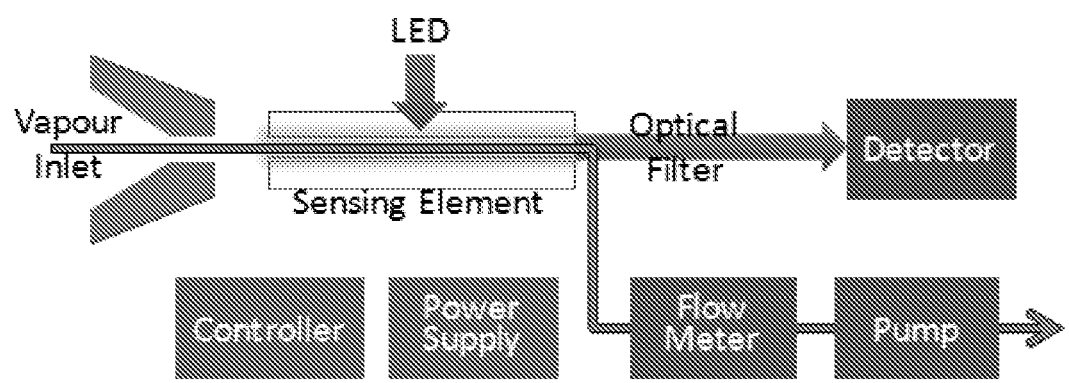

FIG. 8 is a schematic diagram illustrating a device useful in implementing the present invention.

DETAILED DISCUSSION OF THE INVENTION

In accordance with the present invention the presence of hydrogen peroxide (in the vapour phase) can be detected based on the luminescent response of an optical sensing element when exposed to hydrogen peroxide. More specifically, the optical sensing element exhibits a characteristic "turn on" response in the presence of hydrogen peroxide. In the present application what is meant by "turn on" response is that on exposure to hydrogen peroxide the sensing compound of the optical sensing element reacts with the hydrogen peroxide to form what is referred to herein as a "reporter compound". The reporter compound absorbs stimulating radiation at a (predetermined) wavelength and exhibits a luminescent response that can be detected. In contrast, the sensing compound itself does not absorb at the predetermined wavelength for the reporter compound and therefore does not exhibit a luminescent response. The presence of hydrogen peroxide can therefore be determined based on whether this "turn on" luminescent response is detected. The fact that the sensing compound does not absorb at the same predetermined wavelength as the reporter compound enhances the sensitivity of detection by eliminating background luminescence from the sensing compound. When compared with the approach taught in US 2014/0193923A1 the present invention is not restricted to using sensing compounds that absorb at a particular wavelength and do not exhibit a luminescent response at that wavelength. This important difference will be easily understood with reference to the following table.

with hydrogen peroxide to form the reporter compound, absorption by the reporter compound does take place at that wavelength with a related (detectable) luminescent response. This is also a turn-on response in the presence of hydrogen peroxide but the response involves both absorption and emission by the reporter compound. In the context of the present specification a wavelength of 388 nm is a suitable "predetermined wavelength". Whether a particular compound is useful in the present invention may be established by determining the optical properties of the compound in its pristine state and when reacted with hydrogen peroxide. There may be one or more wavelengths at which the requisite turn-on response is exhibited in a reporter molecule whilst at that same wavelength the sensing compound does not absorb.

It will be appreciated that the turn-on response required in US 2014/0193923A1 is fundamentally different from that required in the present invention. The present invention may offer increased flexibility with respect to the range of sensing compounds that may be used because selection of suitable compounds is not constrained by the same criteria as in this US publication, that is, there is no longer the requirement that the sensing compound be non-luminescent.

The "turn on" response of sensing compounds used in accordance with the present invention may also be applied for the detection of organic peroxide compounds that can be decomposed to yield hydrogen peroxide. In this case a sample to be analysed is first processed so that organic peroxide(s) that may be present in the sample are decomposed to yield hydrogen peroxide. Herein the sample following treatment is referred to as a "conditioned sample". If the sample being treated contains one or more organic peroxides, the conditioned sample will include hydrogen peroxide and this can be detected in accordance with the methodology described above. In this case a determination that hydrogen peroxide is present in the conditioned sample indicates the presence of organic peroxide(s) in the sample that has been tested.

| | Selected | Sensing compound | | After reaction with $H_2O_2$ | |
|---|---|---|---|---|---|
| Sensing compound | excitation wavelength/nm | Absorbs? (Yes/No?) | Luminescence (Yes/No?) | Absorbs (Yes/No?) | Luminescence (Yes/No?) |
| US2014/0193923A1 | 340 | Y | N | Y | Y |
| Present invention | 388 | N | N | Y | Y |

In the table the excitation wavelengths are nominally chosen to be 340 nm and 388 nm for purposes of illustration, with the latter chosen in the context of the current inventions such that the sensing compound is not excited.

The compounds used in US 2014/0193923A1 will absorb at a wavelength of 340 nm but there will be no related luminescent emission. However, after reaction with hydrogen peroxide the resultant compound will also absorb at 340 nm and exhibit a detectable luminescent response. This characteristic turn-on response is the basis upon which detection of hydrogen peroxide takes place. It is critical that before exposure to hydrogen peroxide the compounds do not give any (detectable) luminescent response as that would interfere with the luminescent response when the compounds have reacted with hydrogen peroxide.

In contrast, the sensing compound used in the present invention and used as an example in the above table does not absorb at a wavelength of 388 nm and thus does not exhibit any luminescent response when illuminated at that wavelength. However, when the sensing compound is reacted On the other hand, if the sample being tested does not contain any organic peroxide(s), then treatment of the sample will not yield any hydrogen peroxide in the conditioned sample. In this case the "turn on" response will not be observed and from this it can be assumed that organic peroxide(s) is/are not present.

The sensing compound of the optical sensing element used in the present invention is reactive with hydrogen peroxide to produce a luminescent reporter compound that exhibits "turn on" luminescent properties as described. The reaction preferably takes place at room temperature and pressure as this simplifies design of a sensing device in which the sensing compound/optical sensing element is used. However, this is not essential and it is possible that the reaction takes place at elevated temperature and the device designed accordingly to facilitate this. For example, the device may require some form of heating means to raise the temperature of the optical sensing element.

In an embodiment of the invention in the optical sensing element the sensing compound is provided as a thin film coating on a solid transparent substrate. Here the term "transparent" refers to the ability of the substrate to allow transmission of electromagnetic radiation at the predetermined wavelength being used for excitation. In this embodiment the optical sensing element is therefore a solid-state system. The sensing compound will typically be provided as a continuous layer (coating) on transparent substrate. To produce the coating the sensing compound may be dissolved in a solvent and applied to the substrate. The solvent is then removed leaving the sensing compound on the substrate. Examples of suitable solvents that may be useful in practice of the invention include toluene, chlorinated solvents such as dichloromethane, acetone, ethanol, methanol, iso-propanol, tert-butanol, methoxyethanol, tetrahydrofuran (THF), N,N-dimethylformamide (DMF), dimethyl sulfoxide (DMSO), 1,3-dioxane and 1,4-dioxane.

In a preferred embodiment the coating comprising the sensing compound also contains a base. The base is preferably soluble in the solvent used to apply the sensing compound and enable an optically non-scattering film coating to be formed. In the optical sensing element, a base is employed to make a film coating together with the sensing compound. The base is used as a catalyst to enhance the response. Hydrogen peroxide (HOOH) has a pKa of around 11.7. A base of a conjugate acid with suitable pKa would lead to the equilibrium formation of HOO⁻, which is more nucleophilic than HOOH. Furthermore, base can be used to ensure that after removal of boronate the phenolate formed on the reporter compound does not protonate, which leads to the reporter compound absorbing the predetermined wavelength whilst the sensing compound does not. Examples of suitable bases that may be useful in practice of the invention include 4-N,N-dimethylaminopyridine (DMAP), polyethylenimine (PEI), tetramethylammonium hydroxide and tetra (n-butyl ammonium)hydroxide (n-Bu$_4$NOH).

In the optical sensing element, a polymer may also be employed to make a coating together with the sensing compound and base in particular in the scenarios that require large-area and/or thick coatings. Examples of suitable polymers that may be useful in practice of the invention include polyethylenimine (PEI), polyethylene oxide (PEO) and cellulose acetate.

The minimum amount of sensing compound provided in the coating will be that required to produce a detectable luminescent response when the sensing compound is exposed to hydrogen peroxide. The fact that sensing compounds useful in the present invention can give a practically convenient detection response when provided as a coated film on what is effectively a non-porous substrate suggests that the compounds may have greater response sensitivity than compounds taught in US 2014/0193923A1, which require a hydrophilic porous substrate. The latter indicates that the sensing compounds must be provided on a porous substrate to achieve requisite surface area for reaction and air sampling. Furthermore, because the optical sensing element used in the invention uses a non-porous substrate, which may be partially transparent, there is increased flexibility about where and how fluorescence is measured. The approach taught in the US publication referred to is constrained to using an optically scattering and non-transparent sensing element that relies on detection of reflected or scattered light.

The amount of sensing compound included in the coating may be determined experimentally. The thickness of the sensing film will determine how quickly signal saturation is reached with thicker films taking longer and potentially allowing for multiple detection events. Typically, the maximum film thickness is determined such that the reporter compounds formed should absorb nearly all the incident excitation wavelength after all the sensor compounds have reacted with the hydrogen peroxide vapour. In terms of absorbance, it should have an optical density value in the range 1-2 at the excitation wavelength when the response to hydrogen peroxide has reached saturation. In a preferred embodiment the coating thickness will be in the range 0.1 µm-10 µm.

The optical sensing element is generally not reusable due to irreversible reaction with hydrogen peroxide. However, thick films may be used for more than one time in the detection scenarios envisaged and may allow collection of more reliable signal.

Examples of sensing compounds useful in the present invention include boronate esters represented by the following general formula:

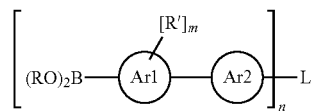

in which:
each R group can be the same or different $C_{2-8}$ alkyl moiety or together with the oxygen atoms to which they are attached form a cyclic structure containing up to 5 carbon atoms, optionally substituted by one or more $C_{1-4}$ alkyl groups;
Ar1 is a (hetero)aromatic moiety and/or comprises fused (hetero)aromatic rings or a chain of (hetero)aromatic or fused (hetero)aromatic rings moieties;
Ar2 is an electron withdrawing group, aromatic unit with electron withdrawing groups attached or a higher electron affinity heteroaromatic moiety;
R' is a solubilising group;
m is an integer equal to 1 or greater;
n is an integer equal to 1 or greater
L is a linker unit that is present when n is greater than 1.

It will be appreciated that the R groups could be protons such that the boron-containing group is a boronic acid, which may also form cyclic species. Preferably, the groups R together with the oxygen atoms to which they are attached form a stable boronate ester.

For example, it is well known that the dimethylboronate ester is easily hydrolysed and hence in a preferred embodiment the R groups form a pinacol ester moiety:

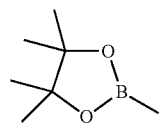

The group Ar1 may be a fluorenyl, bifluorenyl, phenyl, biphenyl, naphthalenyl, anthracenyl, phenanthrenyl, pyrenyl, or perylenyl group. The Ar1 moieties are preferably substituted with R' groups to enhance solubility and the ability to process into optical quality thin films. In a preferred embodiment the presence of the R' groups does not appreciably change the optoelectronic properties of the Ar1 moiety and fluorenyl and bifluorenyl groups are preferred.

For the reporter compound to work successfully the phenolate anion must remain deprotonated. While this can be achieved through the use of strong bases, such bases do not necessarily lead to optical quality films. The pKa of a phenol can be decreased by the attachment of electron withdrawing groups to the aromatic moiety. The presence of the electron-withdrawing moieties can also increase the photostability of the sensing compound, and potentially give faster fluorescence "turn on" kinetics by making the boron more electrophilic. Examples of the group Ar2 include nitro, cyano, phenyl substituted by one or more fluorine, chlorine or bromine atoms, phenyl substituted by one or more haloalkyl groups such as trifluoromethyl, formaldehyde, imine, imidazole, pyrazine, triazole, benzotriazole, thiadiazolebenzotriazole, oxadiazole, oxazole, thiazole, thiadiazole, benzothiadiazole, benzobis(thiadiazole), quinoxaline, and thiodiazoloquinoxaline.

The group R' is intended to facilitate solubilisation of the sensing compound in a solvent thereby allowing the sensing compound to be provided as a film coating on a substrate as described. When more than one R' group is present each R' group may be the same or different. Examples of the group R' include straight or branched chain alkyl groups containing up to 10 carbon atoms (preferably n-propyl groups), ethylene glycol chains including 2-methoxymethyl, 2-methoxyethyl, 2-(2-methoxyethoxy)ethyl, and 2-(2-(2-methoxyethoxy)ethoxy)ethyl, and preferably dendrons that include one or more aryl rings (preferably phenyl) and/or hetero atoms. The use of dendrons enables the tuning of solubility and intermolecular interactions in the solid state, with the latter important in controlling the analyte diffusion, reaction rate, and photoluminescence quantum yield of the sensing material and reporting molecule. The dendrons can be first, second or higher generations, with surface groups chosen to provide the necessary solubility. Thus in a preferred embodiment the sensing compound is a dendrimer comprised of a core, dendrons and surface groups. The boronate groups can be attached to the core, dendrons, or surface groups of the dendrimers although attachment to the core is preferred. The choice of R' group(s) will influence the type of solvent that may be employed and the choice of base.

The integer m is typically 1 to 4.

The integer n is typically 1, 2, 3 or 4 and when L is a polymer then n is typically less than the reactive moieties on the polymer used to connect Ar2.

It has been found that 2-fluorenyl boronic acid pinacol ester compounds are generally useful as sensing compounds in accordance with the invention. Such compounds react with hydrogen peroxide and elicit a "turn on" luminescent response. The reaction involves nucleophilic attack of the HOOH or HOO$^-$ on the boron atom of the boronate ester followed by migration of the bond between the carbon attached to the boron such that there is new bond between the carbon and oxygen atom of the hydrogen peroxide that is attached to the boron atom. The creation of the new functionality with the carbon attached to the oxygen atom leads to the reporter compound whose luminescence is then detected.

Proposed Mechanism:

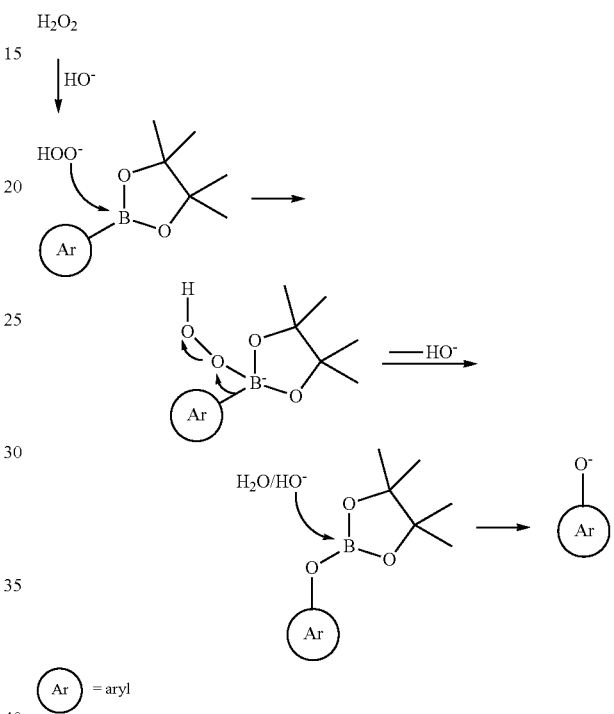

Specific examples of compounds that have been found to be useful in embodiments of the invention are shown below. Compounds are referred to by reference numbers of the form "SQF XXXX" for convenience.

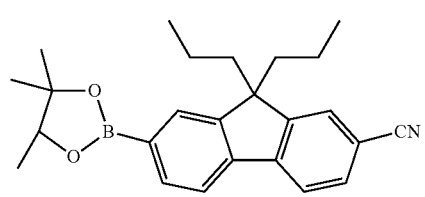

SQF0724

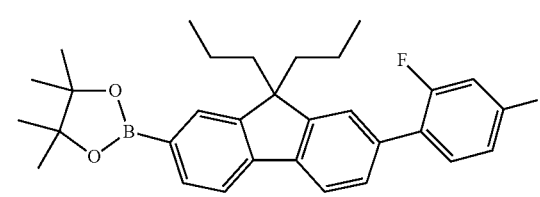

SQF07114

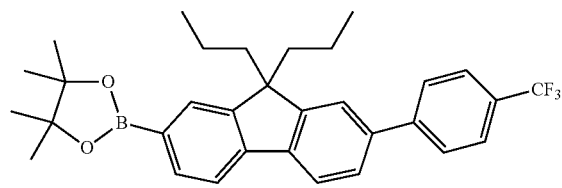

SQF0784

-continued
SQF0756
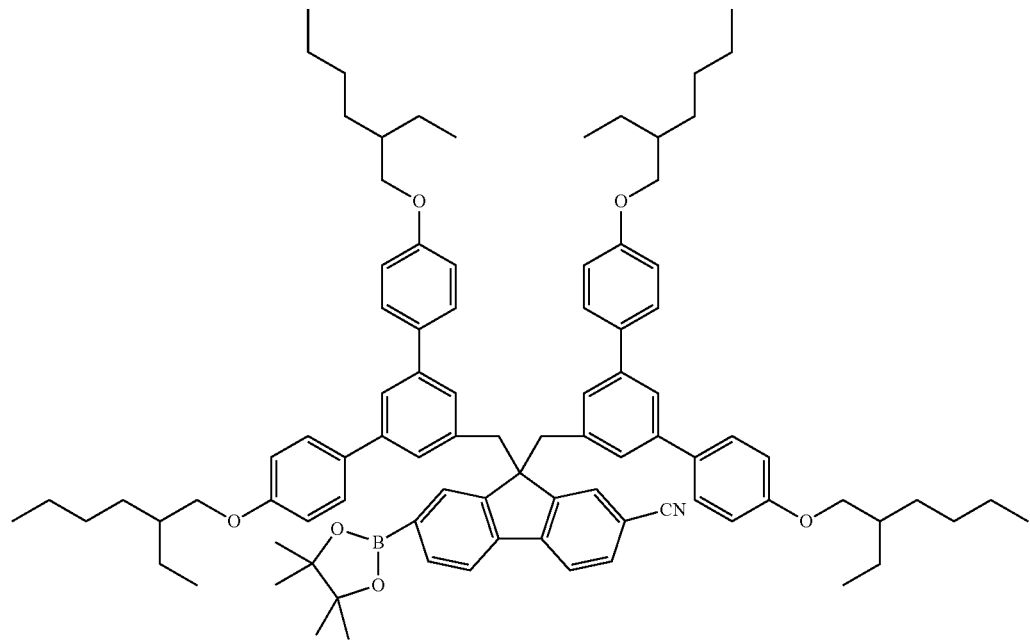
SQF0782
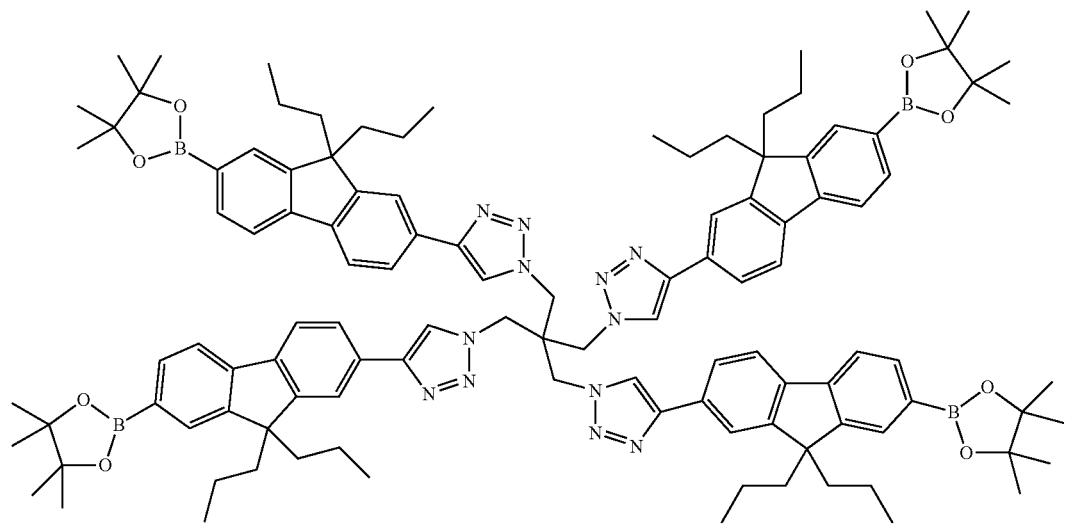

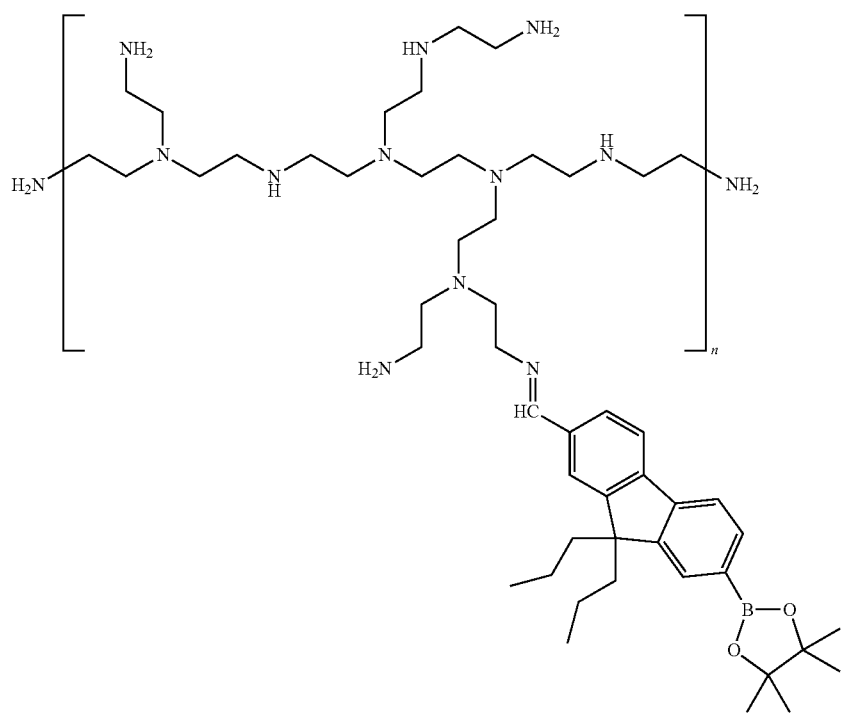

The substrate may take a variety of forms. For example, the transparent substrate may take the form of a tube with the sensing compound provided as a coating on an internal surface of the tube. In this case a sample to be tested is provided to the interior of the tube for contacting where it will come into contact with the sensing compound. The tube may be a capillary tube made of a glass, such as a borosilicate glass or silica. Typically the tube will have an internal diameter of up to 1 mm. The length of the capillary tube is usually no more than 100 mm. Capillary tubes useful in the invention are commercially available and may cut to an appropriate length. A desirable property of the optical sensing element of the invention is that it is non-scattering when irradiated, as takes place during the detection process. Preferred substrates are transparent. However, in certain applications and configurations reflective substrates are also useful.

The minimum amount of sensing compound provided in the coating will be that required to produce a detectable luminescent response when the sensing compound is exposed to hydrogen peroxide. The fact that sensing compounds useful in the present invention can give a practically useful detection response when provided as a coated film on what is effectively a non-porous substrate suggests that the compounds may have greater response sensitivity than compounds taught in US 2014/0193923A1, which require a hydrophilic porous substrate. The latter indicates that the sensing compounds must be provided on a porous substrate to achieve requisite surface area for reaction and air sampling. Furthermore, because the optical sensing element used in the invention uses a non-porous substrate, which may be partially transparent, there is increased flexibility about where and how fluorescence is measured. The approach taught in the US publication referred to is constrained to using an optically scattering and non-transparent sensing element that relies on detection of reflected or scattered light.

The present invention uses an irradiation source for irradiating the optical sensing element with stimulating radiation at a predetermined wavelength. That wavelength is a wavelength at which the reporter compound (formed by reaction of the sensing compound with hydrogen peroxide) absorbs radiation and has a detectable emission. In contrast at that same wavelength the sensing compound itself is not stimulated to emit fluorescence. That is, the predetermined wavelength is chosen such that is equal or greater than the optical gap of the reporter compound but less than the optical gap of the sensing compound. This is the basis upon which the present invention facilitates detection of hydrogen peroxide.

Whether a particular compound exhibits the "turn on" response required to be useful in the present invention may be determined by analysing the optical properties of the sensing compound and the reporter compound (the product formed on reaction of the sensing compound with hydrogen peroxide) at a particular wavelength of irradiation. This involves identifying one or more wavelengths at which the reporter compound can be excited and exhibits a detectable luminescent response, but at which the sensing compound itself is not excited (i.e., does not absorb) and thus does not exhibit a luminescent response. If the "turn on" response is observed for a number of different wavelengths, it may be necessary to select the wavelength based on the intensity of the "turn on" response. It will also be necessary to consider the types of irradiation source available and the wavelength capable of being supplied by the source. Typically, the irradiation source will be a narrowband light source such as a light-emitting diode (LED) or laser. It will also be relevant to consider the type of detector used and its detection sensitivity.

A detector is used for measuring luminescent response of the optical sensing element after exposure to a sample (or conditioned sample). It is envisaged that the luminescent response will be measured with a broadband detector such as a photodiode. To maximize sensitivity an amplified detector such as an avalanche photodiode or photomultiplier tube could be used. Alternatively, a spectrally resolved detector such as CCD spectrograph may be used to resolve changes in the luminescence shape and intensity. In addition, a long-pass or band-pass optical filter should be included between the sensor and the detector to block the excitation wavelength from reaching the detector. The detection will include some means for relating to an operator the luminescence measured by the detector. This means may involve some form of signal, for example a signal that is communicated visually, audibly or stimulatorily (for example by vibration).

The device of the invention will also include a means for delivering a sample to be analysed for contacting with the optical sensing element. The sample will be gaseous. Typically, this means a fan or blower or pump coupled with a flow meter will be needed to continuously draw the sample into contact with the optical sensing element. An example of a device illustrating a device useful in implementing the present invention is illustrated in FIG. 8.

The sensing compound is reactive with hydrogen peroxide but the invention may readily be applied to detecting organic peroxide(s) that can be decomposed to produce hydrogen peroxide. Then detection of hydrogen peroxide, in accordance with the present invention, is indirectly indicative of the presence in the sample of organic peroxide(s). In this case the sample being tested must first be processed in order to cause any organic peroxide(s) in the sample to be decomposed to produce hydrogen peroxide. In order to achieve this, the sample may be contacted with a reagent that will cause decomposition of organic peroxide(s) thereby producing hydrogen peroxide.

Organic peroxide(s) in the sample will be in the vapour phase and decomposition may be achieved using known reagents. Preferably decomposition takes place at room temperature but this is not essential. If elevated temperature is required for the decomposition, the device may include some form of heating means. It is envisaged that the device of the invention will be equipped with built-in/integral means for facilitating decomposition of organic peroxide(s). An alternative would be for a sample to be tested to be processed separately for decomposition of any organic peroxide(s) and generation of a conditioned sample before delivery to the device for detection of hydrogen peroxide.

Decomposition of organic peroxide(s) may be achieved using known methodology. For ease of implementation it is preferred that decomposition is achieved using a solid-state acidic catalyst. Examples of such catalyst are known in the art and include Amberlyst-15. The catalyst may be provided on a suitable substrate at the front end of the device for contacting with a sample to be tested. This step produces what is termed herein as a "conditioned sample". The conditioned sample can then be delivered to the optical sensing element as described for detection of hydrogen peroxide.

In another embodiment a UV irradiation source may be used for decomposing organic peroxide(s) to form the conditioned sample.

In accordance with the invention it may be possible to detect the presence of methyl ethyl ketone peroxide (MEKP), triacetone triperoxide (TATP), diacetone diperoxide (DADP) and hexamethylene triperoxide diamine (HMTD).

Figure 3D:
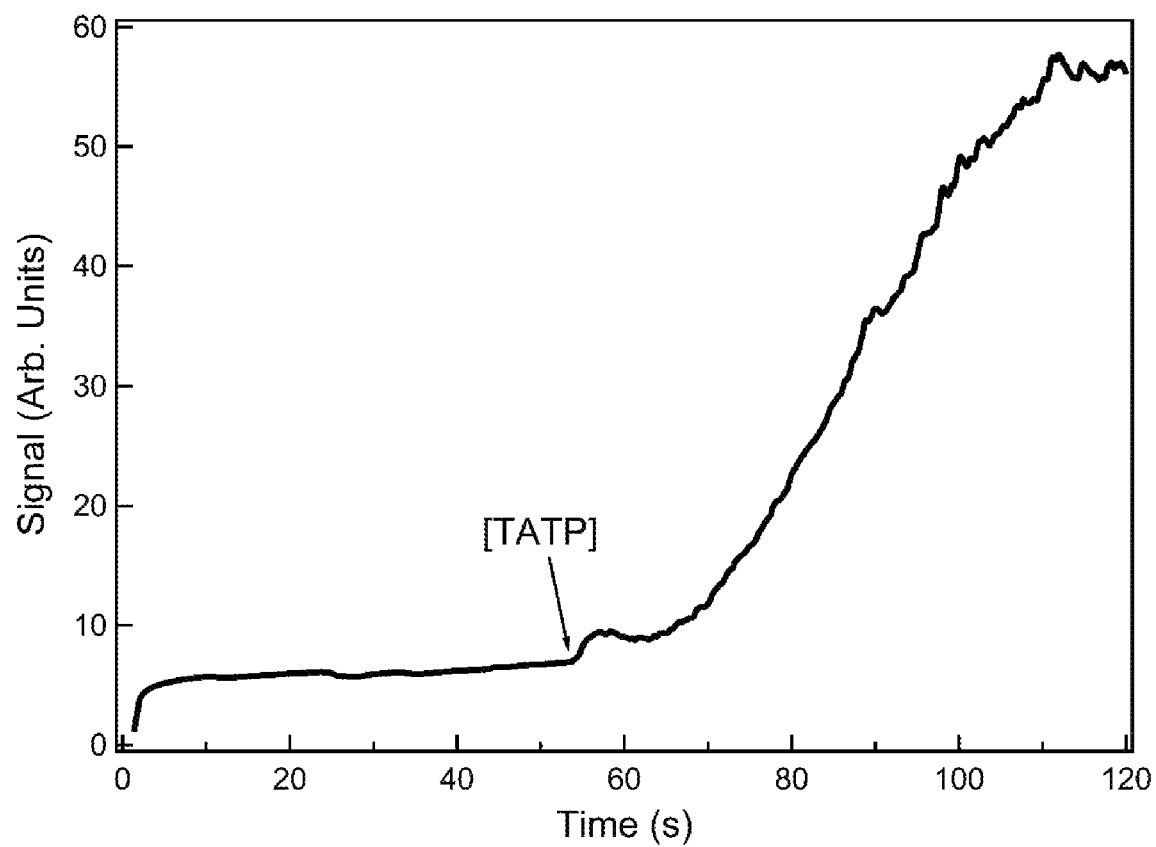
FIG. 3d is a graph showing the PL response of capillary coated internally with a film comprising SQF07114 versus time. Base: n-Bu$_4$NOH (6 eq). [TATP] represents the conditioned sample from TATP generated using Amberlyst-15 as catalyst.
Figure 4:
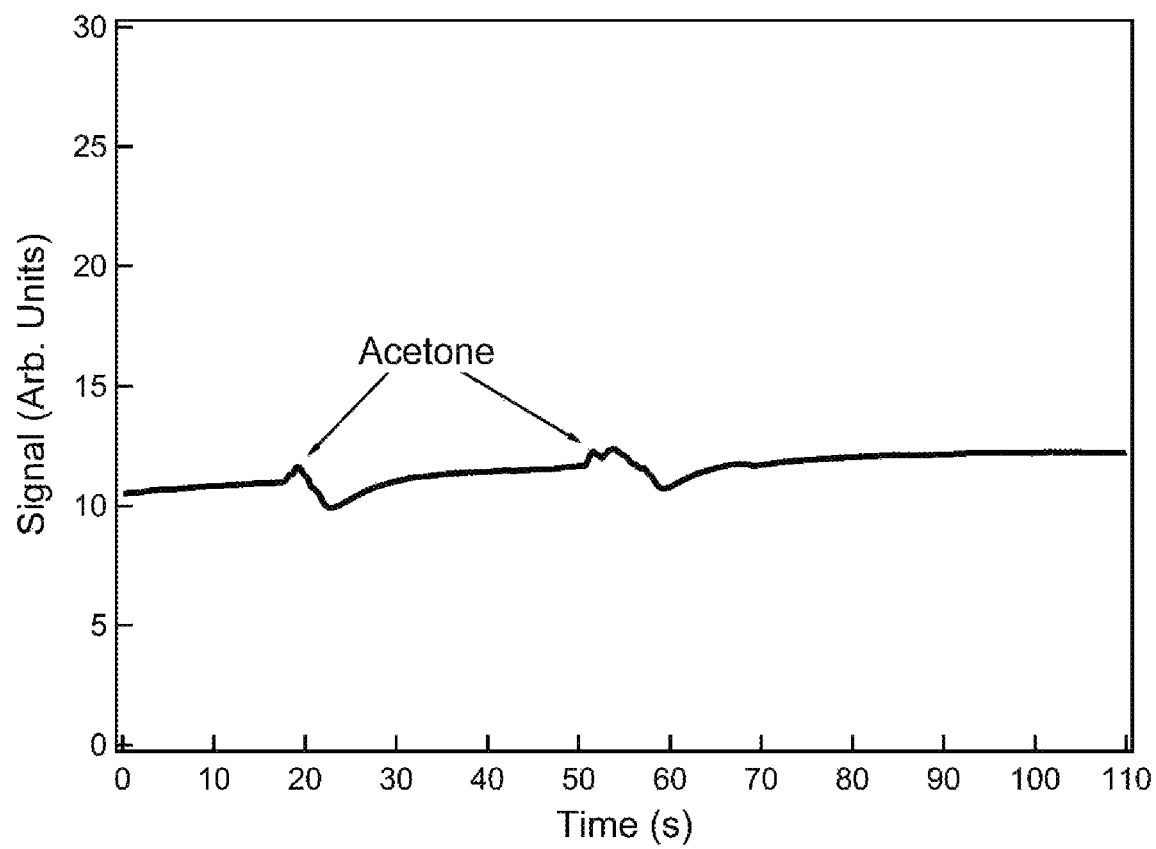
FIG. 4 is a graph showing the PL response of capillary coated internally with a film comprising SQF07114 upon exposing to acetone vapour. Base: n-Bu$_4$NOH (6 eq).

In an embodiment of the invention it has been observed that the luminescent response of the reporter compound may be used to distinguish between a sample that contains an organic peroxide that has been decomposed to yield hydrogen peroxide as part of the detection protocol, and a sample that contains hydrogen peroxide per se. The difference in luminescent response is believed to be due to the presence of one or more reaction by-products when the organic peroxide is decomposed. The one or more reaction by-products may interact with the reporting compound as well the hydrogen peroxide to produce a luminescent response profile that is different from the luminescent response profile when the sensing compound interacts with hydrogen peroxide in the absence of the one or more by-products. For example, when TATP is decomposed, acetone is produced as well as hydrogen peroxide. The mixture of acetone and hydrogen peroxide will result in a different luminescent response profile when compared with that obtained when hydrogen peroxide is present without the acetone. In the case of acetone the luminescent response of the reporter compound temporarily increases, whereas with hydrogen peroxide the luminescent response increases as long as there is hydrogen peroxide reacting with the sensing compound to form new reporter compound. This embodiment may be understood with reference to various figures included herein. FIG. 4 shows a (rapidly) reversible response due to the presence of acetone. FIG. 5 shows the response to hydrogen peroxide in the absence of acetone. FIG. 3d shows an initial (rapidly) reversible response due to the presence of acetone and then the response due to the reaction of the sensing compound with hydrogen peroxide to form more reporter compound.

In an embodiment for the selective detection of organic peroxides, the system for detection would suitably comprise two sensing elements with only one element featuring the means of decomposing the sample to hydrogen peroxide. Hence a hydrogen peroxide source would trigger both sensing elements, but an organic peroxide would trigger only the element with the means for decomposing the organic peroxide, thus providing a clear distinction between organic peroxides and hydrogen peroxide.

In accordance with the invention detection of hydrogen peroxide per se, or detection of hydrogen peroxide as a result of decomposition of organic peroxide(s), may be indicated visually, audibly or stimulatorily. The invention may have application in civilian security applications where detection of explosives is important, for example at airports and stadiums. The invention may also have application in military applications.

The fluorescence "turn on" can be detected rapidly in the measured vapour concentrations of hydrogen peroxide, which is produced from the decomposition of 300 ppb to 8 ppm of TATP. The response time is several seconds. The PL change is dependent on the hydrogen peroxide concentration, which allows determination of the limit of detection (LOD) by extrapolation. LOD varies with the specific sensing compound and 1 ppb of TATP can be achieved. Some common interferents such as perfume give small and reversible signals of PL change. In comparison, hydrogen peroxide gives significantly higher and irreversible PL signals, which can be used to differentiate hydrogen peroxide and conditioned samples from interferents.

Embodiments of the present invention are illustrated with reference to the following non-limiting examples.

EXAMPLES

Example 1: Compound Preparation—Sensing Compounds

The sensing compounds were synthesized following the routes shown in Schemes 1-7. In general the reactive boronate ester was formed from the corresponding bromide via a Miyaura borylation reaction or an aryllithium intermediate. The starting materials were either commercially available or synthesised using reported methods.

[1]: Synthesis of SQF0724

Scheme 1. Synthesis of SQF0724

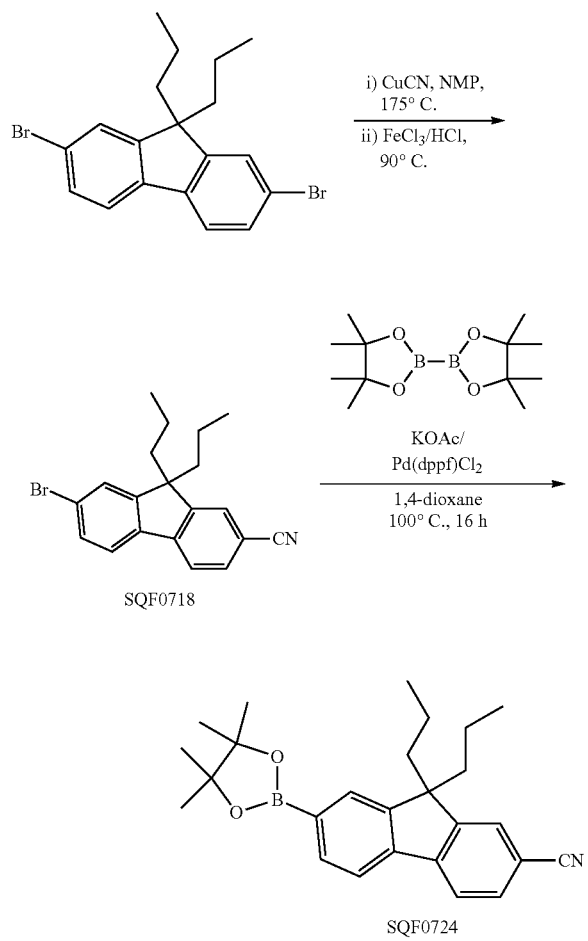

SQF0718

SQF0724

Synthesis of SQF0718
7-bromo-9,9-di-n-propyl-9H-fluorene-2-carbonitrile

A mixture of 2,7-dibromo-9,9-di-n-propylfluorene (4.08 g, 10.0 mmol), CuCN (896 mg, 10.0 mmol) and N-methyl pyrrolidone (NMP) (30 mL) was heated under argon in an oil bath held at 175° C. for 6 h. The mixture was allowed to cool to 120° C. An acidified aqueous $FeCl_3$ solution (6.00 g of $FeCl_3$ in a mixture of 1.5 mL of concentrated HCl and 9 mL of water) was poured slowly onto the hot reaction mixture. The mixture was heated at 90° C. for a further 20 min. The mixture was allowed to cool to room temperature and then 50 mL of water was added. The aqueous layer was then separated from the organic layer, and was extracted with toluene (3×50 mL). All the organic portions were combined, washed sequentially with 6 M HCl (2×50 mL), 10% NaOH solution (2×50 mL), and distilled water (2×100 mL), dried over anhydrous sodium sulphate and filtered. The filtrate was collected and the solvent removed. The residue was purified by column chromatography over silica using ethyl acetate: petroleum ether (1:20-1:4) as eluent to give a white solid (1.88 g, 53%). mp 149-150° C. Elemental analysis (%) calcd for $C_{20}H_{20}BrN$ C, 67.80, H, 5.69, N, 3.95; Found: C, 68.17, H, 5.80, N, 3.96. $\lambda_{max}$(dichloromethane)/nm: 282 sh (log $\varepsilon$/dm$^3$ mol$^{-1}$ cm$^{-1}$ 4.23), 293 (4.33), 306 (4.22), 318 (4.41). $^1$H NMR (400 MHz, CDCl$_3$) δ7.73 (1H, dd, J=8 & 1), 7.63 (1H, dd, J=8 & 1.5), 7.59-7.61 (2H, m), 7.49-7.52 (2H, m), 1.95 (4H, t, J=8), 0.56-0.78 (m, 10H). $^{13}$C NMR (100 MHz, CDCl$_3$) δ153.5, 151.1, 144.5, 138.1, 131.4, 130.6, 126.5, 126.5, 123.2, 122.1, 120.3, 119.6, 110.4, 56.0, 42.3, 17.1, 14.2. m/z [ESI$^+$]: 376 ([M+Na]$^+$).

Synthesis of SQF0724 9,9-di-n-propyl-7-(4,4,5,5-tetramethyl-1,3,2-dioxaborolan-2-yl)-9H-fluorene-2-carbonitrile A mixture of 7-bromo-9,9-di-n-propylfluorene-2-carbonitrile (886 mg, 2.5 mmol), bis(pinacolato)diboron (762 mg, 3.0 mmol), potassium acetate (736 mg, 7.5 mmol), [1,1-bis(diphenylphosphino)ferrocene] palladium(II) dichloride dichloromethane complex (55 mg, 0.075 mmol) and 1,4-dioxane (30 mL) was heated under argon in an oil bath held at 100° C. for 16 h. The mixture was allowed to cool to room temperature and then the solvent removed under reduced pressure. Water (50 mL) and dichloromethane (50 mL) was added to the reaction and the organic phase was separated. The aqueous layer was extracted with dichloromethane (3×30 mL). The dichloromethane extracts were combined, washed with brine (2×50 mL), dried over anhydrous sodium sulfate, and filtered. The filtrate was collected and the solvent removed. The residue was purified by column chromatography over silica using ethyl acetate: petroleum ether (1:20-1:6) as eluent to give a white solid (664 mg, 66%). mp 151-152° C.; mp (DSC)=156° C. (DSC scan rate 50° C./min); mp (TGA)=158° C. (TGA scan rate 50° C./min); $T_{5\% decomp}$=273° C. (sublimed); Tg=61° C. (DSC scan rate 100° C./min). Elemental analysis (%) cal. for $C_{26}H_{32}BNO_2$: C, 77.8; H, 8.0; N, 3.5. Found: C, 77.8; H, 8.1; N, 3.4. $\lambda_{max}$(dichloromethane)/nm: 285 sh (log $\varepsilon$/dm$^3$ mol$^{-1}$ cm$^{-1}$ 4.35), 294 (4.45), 308 (4.34), 315 sh (4.33), 321 (4.51). $\lambda_{max}$(em) (dichloromethane)/nm: 341, 356 sh, 374 sh. $^1$H NMR (500 MHz, CDCl$_3$) δ 7.84 (1H, dd, J=7.5 & 1), 7.77-7.79 (2H, m), 7.73 (1H, dd, J=7.5 & 0.5), 7.62 (1H, dd, J=7 & 1.5), 7.62 (1H, s), 1.89-2.17 (4H, m), 1.39 (12H, s), 0.51-0.68 (10H, m). $^{13}$C NMR (125 MHz, CDCl$_3$) δ 152.0, 150.5, 145.5, 141.9, 134.0, 131.2, 129.0, 126.6, 120.6, 120.0, 119.8, 110.3, 84.0, 55.7, 42.3, 24.9, 17.1, 14.3.

m/z [ESI$^+$]: 440 ([M+K]$^+$).

[2]: Synthesis of Dendrimer SQF0756

Schene 2, Synthesis of SQF0756

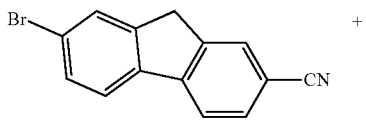

+

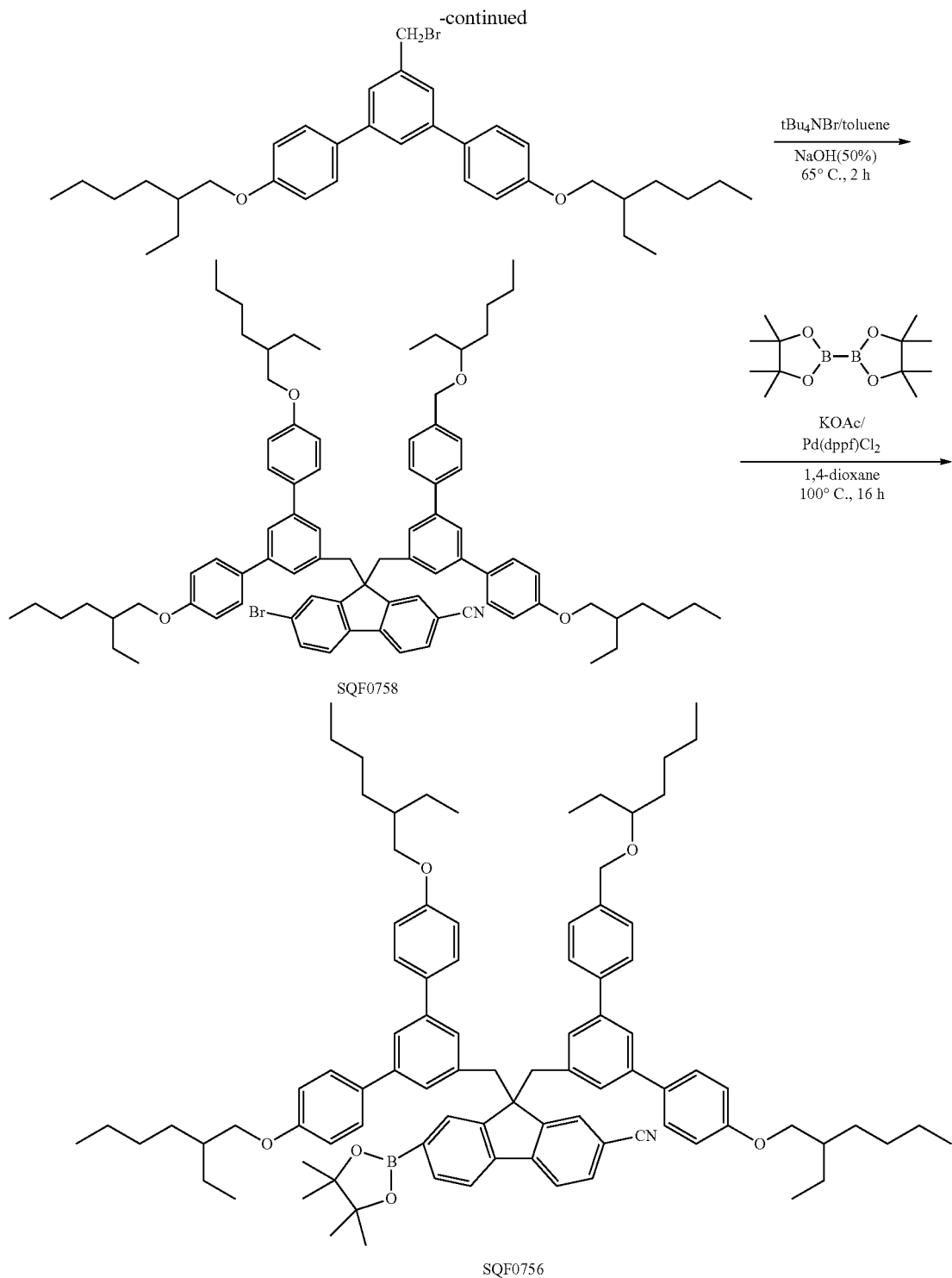

Synthesis of SQF0758 9,9-bis((4,4''-bis((2-ethylhexyl)oxy)-[1,1':3',1''-terphenyl]-5'-yl)methyl)-7-bromo-9H-fluorene-2-carbonitrile A mixture of 7-bromo-9H-fluorene-2-carbonitrile (42 mg, 0.15 mmol), tert-butylammonium bromide (12 mg, 0.038 mmol), and toluene (4 mL) was placed in 50 mL RBF, and then placed under vacuum and then backfilled with argon three times. Then 4 mL of NaOH (50%) was purged with $N_2$ for 10 min and added to the above mixture. The resultant mixture was then placed under vacuum and backfilled with argon three times before being heated in an oil bath at 65° C. for 15 min. Then 5'-(bromomethyl)-4,4''-bis((2-ethylhexyl)oxy)-1,1':3',1''-terphenyl (260 mg, 0.45 mmol) was quickly added under $N_2$ stream and the resultant mixture was kept in the oil bath held at 65° C. for another 2 h. After cooling to room temperature, 30 mL of toluene was added, washed by water (3×30 mL), brine (2×50 mL), dried over sodium sulphate and filtered. The filtrate was collected and the solvent was removed in vacuo to give solids. The crude was purified by column chromatography over silica using dichloromethane:petroleum ether (2:3) to give the product as white solid (174 mg, 91%). mp ° C. (167-168° C.). Elemental analysis (%) calcd for $C_{84}H_{100}BrNO_4$ C, 79.6, H, 8.0, N, 1.1; Found: C, 79.7, H, 8.1, N, 1.0. $\lambda_{max}$(dichloromethane)/nm: 270 (log ε/dm$^3$ mol$^{-1}$ cm$^{-1}$ 4.98), 318 (4.14). $^1$H NMR (δ, 400 MHz, CDCl$_3$): 7.98 (1H, d, J=1, Fl-H), 7.92 (1H, d, J=1.5, Fl-H), 7.59 (1H, dd, J=8 & 1.5, Fl-H), 7.50 (1H, dd, J=8 & 2, Fl-H), 7.43 (1H, d, J=8, Fl-H), 7.35 (2H, dd, J=1.5, Ph-H), 7.31 (1H, d, J=8, Fl-H), 7.21-7.24 (8H, m, Ph-H), 6.91-6.95 (8H, m, Ph-H), 6.79 (2H, d, J=1, Ph-H), 3.84-3.88 (8H, m, OAlkyl-H), 3.51-3.58 (4H, m, Ph-CH$_2$), 1.72-1.78 (4H, m, OAlkyl-H), 1.32-1.57 (32H, m, OAlkyl-H), 0.91-0.97 (24H, m, OAlkyl-CH$_3$). $^{13}$C NMR (δ, 100 MHz, CDCl$_3$): 159.0, 151.4, 149.2, 144.6, 140.5, 138.3, 136.2, 133.0, 131.7, 131.0, 128.6, 128.3, 128.0, 127.0, 123.3, 122.6, 122.5, 120.7, 119.3, 114.7, 109.7, 70.5, 58.1, 45.1, 39.4, 30.5, 29.1, 23.9, 23.1, 14.1, 11.1. MS (ESI): m/z found: 1290 (M+Na$^+$).

Synthesis of SQF0756

9,9-bis((4,4''-bis((2-ethylhexyl)oxy)-[1,1':3',1''-terphenyl]-5'-yl)methyl)-7-(4,4,5,5-tetramethyl-1,3,2-dioxaborolan-2-yl)-9H-fluorene-2-carbonitrile A mixture of 9,9-bis((4,4''-bis((2-ethylhexyl)oxy)-[1,1':3',1''-terphenyl]-5'-yl)methyl)-7-bromo-9H-fluorene-2-carbonitrile (39 mg, 0.03 mmol), bis(pinacolato)diboron (15 mg, 0.06 mmol), potassium acetate (10 mg, 0.10 mmol), and 1,1'-bis(diphenylphosphino)ferrocene-palladium(II)-dichloride dichloromethane complex (4 mg, 0.004 mmol) was placed in a 10 mL round-bottom flask, vacuumed for 1 h and then backfilled with Ar(g). Then anhydrous 1,4-dioxane (2 mL) was added and the resulting mixture was heated at 105° C. for 16 h under Ar(g) protection. After cooling to room temperature, 1,4-dioxane was removed under vacuo and the residue was purified by column chromatography over silica using dichloromethane:petroleum ether (1:1 to 1:0) as eluent to afford the product as a white solid (25 mg, 63%). mp 102-103° C. Tg=76° C. (DSC scan rate 100° C./min); T$_5$% (decomp.)=369° C. Elemental analysis (%) calcd for $C_{90}H_{112}BNO_6$ C, 82.22, H, 8.59, N, 1.07; Found: C, 82.16, H, 8.64, N, 0.98. $\lambda_{max}$(dichloromethane)/nm: 270 (log ε/dm$^3$ mol$^{-1}$ cm$^{-1}$ 5.04), 320 sh (4.17). $\lambda_{max}$(em) (dichloromethane)/nm: 422. $^1$H NMR (δ, 400 MHz, CDCl$_3$): 8.29 (1H, s, Fl-H), 7.94 (1H, s, Fl-H), 7.86 (1H, d, J=7.5, Fl-H), 7.55 (1H, d, J=8, Fl-H), 7.48 (2H, d, J=7, Fl-H), 7.29 (2H, s, Ph-H), 7.14-7.17 (8H, AA'BB', Ph-H), 6.88-6.90 (8H, AA'BB', Ph-H), 6.76 (4H, s), (2H, d, J=1, Ph-H), 3.82-3.88 (8H, m, OAlkyl-H), 3.57-3.64 (4H, m, Ph-CH$_2$), 1.71-1.77 (4H, m, OAlkyl-H), 1.33-1.57 (44H, m, OAlkyl-H & BOCH$_3$), 0.90-0.96 (24H, m, OAlkyl-CH$_3$). $^{13}$C NMR (δ, 100 MHz, CDCl$_3$): 158.9, 149.6, 148.7, 145.6, 142.2, 140.3, 136.7, 134.4, 133.2, 131.5, 131.1, 128.5, 127.9, 127.1, 123.1, 121.1, 120.5, 119.5, 114.6, 109.5, 84.0, 70.5, 58.9, 45.1, 39.4, 30.5, 29.1, 24.9, 23.9, 23.1, 14.1, 11.1. MS (ESI): m/z found: 1336 (M+Na$^+$).

[3]: Synthesis of SQF0782

Scheme 3. Synthesis of SQF0782

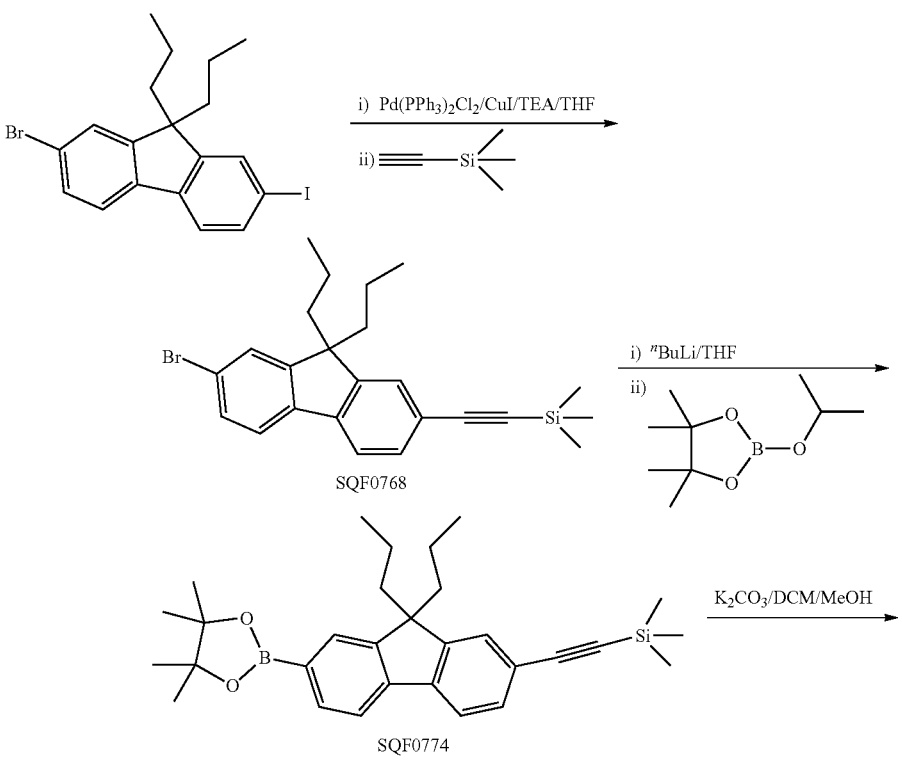

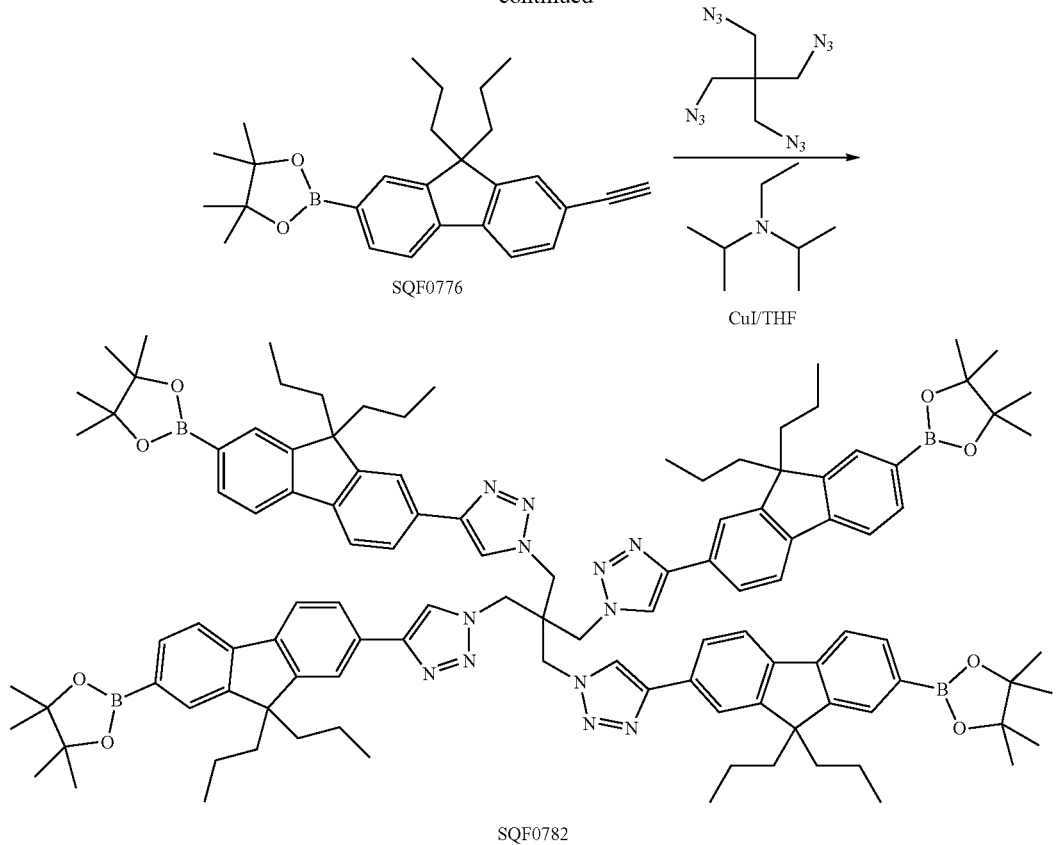

Synthesis of SQF0768 ((7-bromo-9,9-di-n-propyl-9H-fluoren-2-yl)ethynyl)trimethylsilane 2-Bromo-7-iodo-9,9-dipropyl-9H-fluorene (2.0 g, 4.39 mmol) was placed in a 100 mL round-bottom flask, placed under vacuum for 1 h and backfilled with argon. Then anhydrous tetrahydrofuran (30 mL) and dried triethylamine (5 mL) were added. The resultant mixture was placed under vacuum and backfilled with argon three times. Then copper (I) iodide (33 mg, 0.18 mmol) and bis(triphenylphosphine)palladium(II) dichloride (62 mg, 0.09 mmol) were quickly added. The resultant mixture was vacuumed and backfilled with argon six times. Trimethylsilylacetylene (0.63 mL, 4.39 mmol) was injected via syringe and the solution was stirred at room temperature for 3 h. Then the mixture was filtered through a Celite pad, the filtrate was concentrated by vacuo and purified by column chromatography over silica using petroleum ether as eluent to give the product as gum-like semisolid (1.49 g, 80%). mp 107-108° C. Elemental analysis (%) calcd for $C_{24}H_{29}BrSi$ C, 67.8, H, 6.9; Found: C, 67.5, H, 6.9. $\lambda_{max}$(dichloromethane)/nm: 291 sh (log $\varepsilon$/dm$^3$ mol$^{-1}$ cm$^{-1}$ 4.48), 300 (4.63), 312 (4.51), 320 sh (4.51), 326 (4.76). $^1$H NMR ($\delta$, 400 MHz, CDCl$_3$): 7.58 (1H, dd, J=8 & 0.5), 7.52 (1H, dd, J=8 & 0.5), 7.42-7.46 (4H, m), 1.86-1.97 (4H, m), 0.58-0.69 (10H, m), 0.28 (9H, s). $^{13}$C NMR ($\delta$, 100 MHz, CDCl$_3$): 153.2, 150.2, 140.4, 139.4, 131.3, 130.1, 126.3, 126.2, 121.8, 121.6, 121.3, 119.5, 105.9, 94.3, 55.6, 42.5, 17.0, 14.3, 0.0(2). MS (ESI): m/z found: 425 (M+H$^+$).

Synthesis of SQF0774

((9,9-di-n-propyl-7-(4,4,5,5-tetramethyl-1,3,2-dioxaborolan-2-yl)-9H-fluoren-2-yl)ethynyl)trimethylsilane A mixture of ((7-bromo-9,9-di-n-propyl-9H-fluoren-2-yl)ethynyl)trimethylsilane (958 mg, 2.24 mmol) and anhydrous tetrahydrofuran (20 mL) was placed in a 100 mL round-bottom flask and then n-butyl lithium (1.2 M, 2 mL) was added dropwise under argon. The mixture was stirred at −78° C. for another 1 h. Then 2-iso-propoxy-4,4,5,5-tetramethyl-1,3,2-dioxaborolane (0.55 mL, 2.70 mmol) was added dropwise and the resultant mixture was stirred at −78° C. for 30 min, then allowed to rise to room temperature and stirred for another 5 h at this temperature. Then 30 mL of water was added and the organic layer was separated. The aqueous layer was extracted by ethyl acetate (3×30 mL). The combined organic layers were washed by brine (2×50 mL), dried over magnesium sulfate, filtered and solvent removed under vacuo. The residue was purified by column chromatography over silica using dichloromethane:petroleum ether (1:2) as eluent to afford the product as a white solid (490 mg, 46%). mp 232-233° C. Elemental analysis (%) calcd for $C_{30}H_{41}BO_2Si$ C, 76.3, H, 8.8; Found: C, 76.1, H, 9.0. $\lambda_{max}$(dichloromethane)/nm: 291 sh (log $\varepsilon$/dm$^3$ mol$^{-1}$ cm$^{-1}$ 4.42), 301 (4.58), 315 (4.55), 324 sh (4.54), 329 (4.77). $^1$H NMR ($\delta$, 400 MHz, CDCl$_3$): 7.80 (1H, dd, J=7.5 & 1), 7.74 (1H, s), 7.67 (1H, dd, J=7.5 & 0.5), 7.62-7.65 (1H, m), 7.44-7.46 (2H, m), 1.89-2.03 (4H, m), 1.39 (12H, s), 0.56-0.67 (10H, m), 0.29 (9H, s). $^{13}$C NMR ($\delta$, 100 MHz, CDCl$_3$): 151.3, 150.2, 143.3, 141.4, 133.8, 131.1, 128.8, 126.3, 121.7, 119.9, 119.3, 106.2, 94.1, 83.8, 55.4, 42.5, 24.9, 17.0, 14.3, 0.0(5). MS (ESI): m/z found: 495 (M+Na$^+$).

Synthesis of SQF0776

2-(7-ethynyl-9,9-di-n-propyl-9H-fluoren-2-yl)-4,4,5,5-tetramethyl-1,3,2-dioxaborolane A mixture of anhydrous potassium carbonate (690 mg, 5.0 mmol) in 20 mL of methanol was stirred at room temperature for 10 min. Then a mixture of ((9,9-di-n-propyl-7-(4,4,5,5-tetramethyl-1,3,2-dioxaborolan-2-yl)-9H-fluoren-2-yl)ethynyl)trimethylsilane (472 mg, 1.0 mmol) in 20 mL of dichloromethane was added. The resultant mixture was placed under vacuum and backfilled with argon three times and then stirred at room temperature for 4 h under argon protection. Then 50 mL of water and 10 mL of brine were added and the organic layer was separated. The aqueous layer was extracted by dichloromethane (3×30 mL). The organic layers were combined, dried with sodium sulfate, filtered and then solvent removed under vacuo. The residue was purified by column chromatography over silica using dichloromethane as eluent to afford the product as a white solid (240 mg, 60%). mp 140-141° C. Elemental analysis (%) calcd for $C_{27}H_{33}BO_2$ C, 81.0, H, 8.3; Found: C, 80.9, H, 8.5. $\lambda_{max}$(dichloromethane)/nm: 287 (log ε/dm$^3$ mol$^{-1}$ cm$^{-1}$ 4.44), 296 (4.57), 310 (4.45), 318 sh (4.46), 324 (4.70). $^1$H NMR (δ, 400 MHz, CDCl$_3$): 7.81 (1H, dd, J=7.5 & 1), 7.76 (1H, s), 7.66-7.70 (2H, m), 7.49 (1H, s), 7.48 (1H, dd, J=7.5 & 1.5), 3.15 (1H, s), 1.90-2.04 (4H, m), 1.39 (12H, s), 0.55-0.68 (10H, m), 0.29 (9H, s). $^{13}$C NMR (δ, 100 MHz, CDCl$_3$): 151.3, 150.2, 143.1, 141.6, 133.8, 131.0, 128.8, 126.6, 120.6, 120.0, 119.3, 84.6, 83.8, 77.2, 55.3, 42.5, 24.9, 17.0, 14.3. MS (ESI): m/z found 423 (M+Na$^+$).

Synthesis of SQF0782

1,1'-(2,2-bis((4-(9,9-di-n-propyl-7-(4,4,5,5-tetramethyl-1,3,2-dioxaboroan-2-yl)-9H-fluoren-2-yl)-1H-1,2,3-triazol-1-yl)methyl)propane-1,3-diyl)bis(4-(9,9-di-n-propyl-7-(4,4,5,5-tetramethyl-1,3,2-dioxaborolan-2-yl)-9H-fluoren-2-yl)-1H-1,2,3-triazole)

A mixture of 2-(7-ethynyl-9,9-dipropyl-9H-fluoren-2-yl)-4,4,5,5-tetramethyl-1,3,2-dioxaborolane (800 mg, 2.0 mmol), 1,3-diazido-2,2-bis(azidomethyl)propane (48 mg, 0.2 mmol) and copper(I) iodide (380 mg, 2.0 mmol) was placed in a 50 mL round-bottom flask then dried under high vacuum for 30 min. Then anhydrous tetrahydrofuran (10 mL) was added, placed under vacuum and backfilled with argon three times. Then 2.8 mL of di-iso-propylethylamine was added and the mixture was placed under vacuum and backfilled with argon three times. The mixture was stirred at room temperature for 20 h under the protection of argon. Then the mixture was diluted with 100 mL tetrahydrofuran and passed through a short plug of Celite, washed with another 100 mL of tetrahydrofuran. The filtrate was collected and solvent removed under vaccuo. The di-iso-propylethylamine in the residue was removed by high vacuum. The residue was purified by column chromatography over silica gel using dichloromethane:ethyl acetate (10:0 to 10:1) as eluent to afford the product as a white solid (266 mg, 72%). mp 248-250° C. $T_{5\% decomp}$=363° C.; Tg=218° C. (DSC scan rate 100° C./min). Elemental analysis (%) calcd for $C_{113}H_{140}B_4N_{12}O_8$ C, 73.9, H, 7.7, N, 9.2; Found: C, 73.9, H, 7.6, N, 8.9. $\lambda_{max}$(dichloromethane)/nm: 289 sh (log ε/dm$^3$ mol$^{-1}$ cm$^{-1}$ 5.02), 297 sh (5.11), 302 (5.14), 319 sh (5.17), 330 (5.24). $\lambda_{max}$(em) (dichloromethane)/nm: 352, 365 sh, 387 sh, 408 sh. $^1$H NMR (δ, 400 MHz, CDCl$_3$): 8.64 (1H, s), 7.98 (1H, s), 7.77-7.83 (4H, m), 7.72 (1H, d, J=7.5), 4.63 (2H, s), 2.05 (4H, m), 1.39 (12H, s), 0.65 (10H, m). $^{13}$C NMR (δ, 100 MHz, CDCl$_3$): 152.3, 150.1, 147.9, 143.4, 141.5, 133.8, 128.9, 128.8, 127.7, 124.8, 124.2, 120.6, 120.1, 119.1, 83.8, 55.6, 49.2, 47.6, 42.6, 24.9, 17.1, 14.4. HRMS (ESI): m/z [M+Na]$^+$1860.1215, found 1860.1215.

[4]: Synthesis of SQF0784

Scheme 4. Synthesis of SQF0784

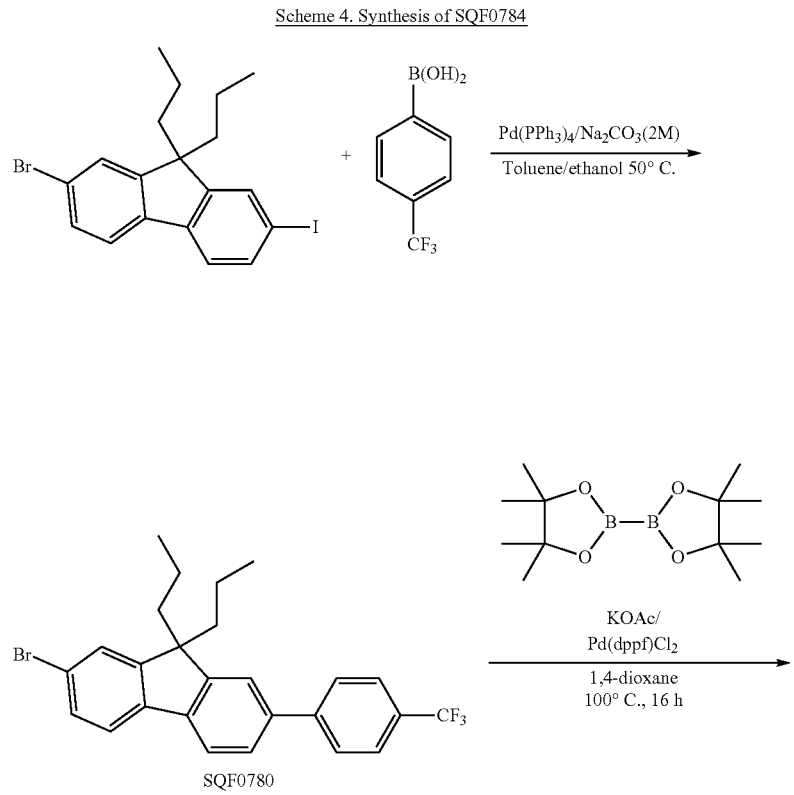

SQF0780

-continued

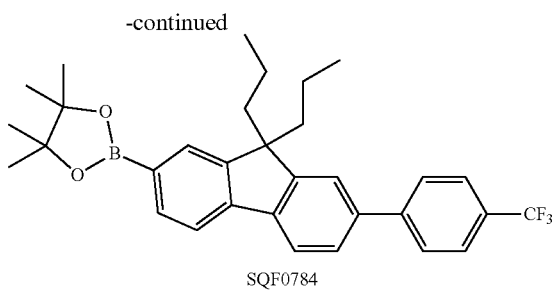

SQF0784

Synthesis of SQF0780 2-bromo-9,9-di-n-propyl-7-(4-(trifluoromethyl)phenyl)-9H-fluorene A mixture of (4-(trifluoromethyl)phenyl)boronic acid (480 mg, 2.53 mmol), 2-bromo-7-iodo-9,9-di-n-propyl-9H-fluorene (1.38 g, 3.03 mmol), sodium carbonate (5.3 g, 50 mmol), toluene (100 mL), ethanol (25 mL) and water (25 mL) was placed in a 250 mL round-bottom flask, placed under vacuum and then backfilled with Ar(g) six times. Then tetrakis(triphenylphosphine)palladium(0) (500 mg, 0.43 mmol) was added and the resulting mixture was placed under vacuum and then backfilled with Ar(g) six times. The mixture was held in an oil bath at 50° C. for 36 h under argon protection. After cooling to room temperature, 50 mL of ethyl acetate and 50 mL of water were added and the layers were separated. The aqueous phase was extracted with ethyl acetate (3×50 mL), and the combined organic phases were washed with brine (2×100 mL), dried over NaSO$_4$, filtered, and evaporated in vacuo. The residue was purified by column chromatography over silica using ethyl acetate: petroleum ether (1:19) as eluent to afford the product as a light white solid (1.08 g, 90%). mp 141-142° C. Elemental analysis (%) calcd for C$_{26}$H$_{24}$BrF$_3$ C, 65.97, H, 5.11; Found: C, 65.87, H, 4.86. $\lambda_{max}$(dichloromethane)/nm: 288 sh (log ε/dm$^3$ mol$^{-1}$ cm$^{-1}$ 4.38), 300 (4.48), 321 (4.55). $^1$H NMR (δ, 400 MHz, CDCl$_3$): 7.71-7.77 (5H, m), 7.57-7.60 (2H, m), 7.55 (1H, m), 7.51 (1H, m), 7.48 (1H, dd, J=8 & 2), 1.93-2.04 (4H, m), 0.68-0.74 (10H, m). $^{13}$C NMR (δ, 100 MHz, CDCl$_3$): 153.3, 151.3, 144.9, 140.2, 139.4, 139.0, 130.1, 129.3 ($^2J_{C-F}$=32.3, q), 127.4, 126.4, 126.3, 125.7 ($^3J_{C-F}$=3.6, q), 124.3 ($^1J_{C-F}$=270.2), 121.6, 121.4, 121.2, 120.2, 55.7, 42.6, 17.2, 14.4. MS (APCI): m/z found: 473.4 ([M+H]$^+$).

Synthesis of SQF0784 2-(9,9-di-n-propyl-7-(4-(trifluoromethyl)phenyl)-9H-fluoren-2-yl)-4,4,5,5-tetramethyl-1,3,2-dioxaborolane A mixture of 2-bromo-9,9-di-n-propyl-7-(4-(trifluoromethyl)phenyl)-9H-fluorene (886 mg, 2.5 mmol), bis(pinacolato)diboron (762 mg, 3.0 mmol), potassium acetate (736 mg, 7.5 mmol), [1,1-bis(diphenylphosphino)ferrocene] palladium(II) dichloride dichloromethane complex (55 mg, 0.03 mmol) and 1,4-dioxane (30 mL) was heated under argon in an oil bath held at 100° C. for 16 h. The mixture was allowed to cool to room temperature and then the solvent removed under reduced pressure. Water (50 mL) and dichloromethane (50 mL) was added to the reaction and the organic phase was separated. The aqueous layer was extracted with dichloromethane (3×30 mL). The dichloromethane extracts were combined, washed with brine (2×50 mL), dried over anhydrous sodium sulfate, and filtered. The filtrate was collected and the solvent removed. The residue was purified by column chromatography over silica using ethyl acetate:petroleum ether (1:20-1:6) as eluent to give a white solid (664 mg, 66%). mp 168-169° C.; mp (TGA)=169° C. (TGA scan rate 50° C./min); T$_{5\% \ decomp}$=287° C. (sublimed); Tg=73° C. (DSC scan rate 100° C./min). Elemental analysis (%) cal. for C$_{32}$H$_{36}$BF$_3$O$_2$ C, 73.85; H, 6.97. Found: C, 73.67; H, 7.00. $\lambda_{max}$(dichloromethane)/nm: 290 sh (log ε/dm$^3$ mol$^{-1}$ cm$^{-1}$ 4.39), 300 (4.49), 323 (4.60). $\lambda_{max}$(em) (dichloromethane)/nm: 350, 365, 381 sh, 402 sh. $^1$H NMR (500 MHz, CDCl$_3$) δ 7.83 (1H, d, J=7), 7.80 (1H, d, J=7.5), 7.76-7.78 (3H, m), 7.71-7.74 (3H, m), 7.58 (1H, dd, J=8 & 1.5), 7.56 (1H, m), 1.97-2.08 (4H, m), 1.40 (12H, s), 0.67-0.70 (10H, m). $^{13}$C NMR (100 MHz, CDCl$_3$) δ 152.2, 150.2, 145.1, 143.3, 141.1, 139.0, 133.9, 129.1 ($^2J_{C-F}$=31.4, q), 128.9, 127.5, 126.1, 125.7 ($^3J_{C-F}$=3.6, q), 124.3 ($^1J_{C-F}$=270.2), 121.7, 120.5, 119.2, 83.8, 55.5, 42.6, 24.9, 17.2, 14.4. m/z [ESI$^+$]: 521 ([M+H]$^+$).

[5]: Synthesis of SQF07114

Scheme 5. Synthesis of SQF07114

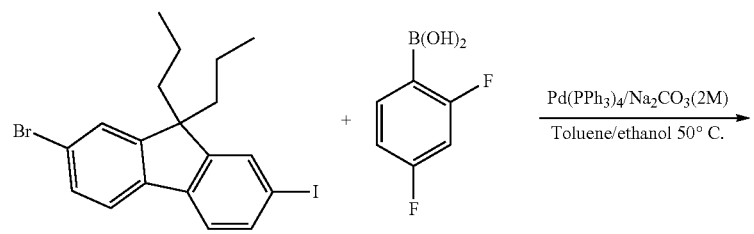

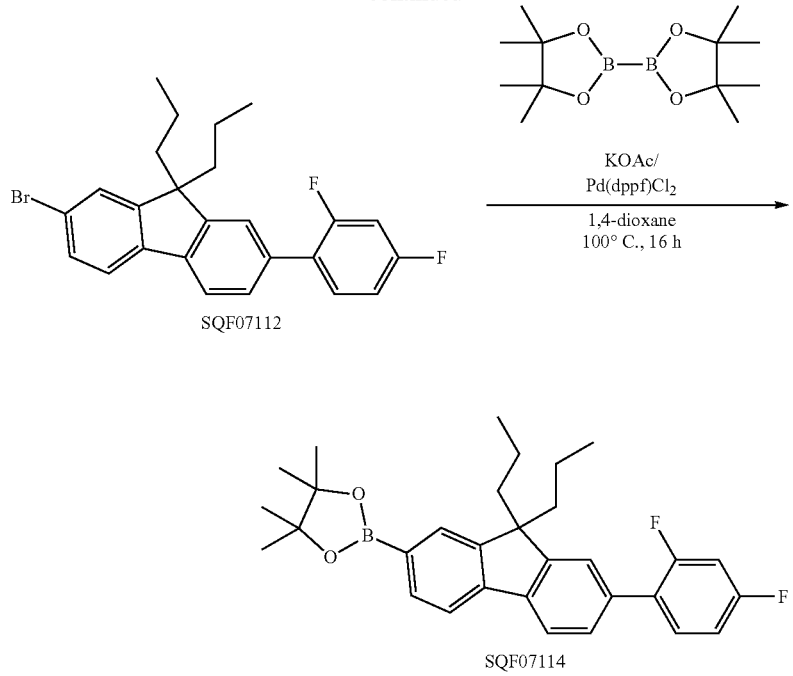

Synthesis of SQF07112 2-bromo-7-(2,4-difluorophenyl)-9,9-di-n-propyl-9H-fluorene A mixture of (2,4-difluorophenyl)boronic acid (316 mg, 2.0 mmol), 2-bromo-7-iodo-9,9-di-n-propyl-9H-fluorene (1.10 g, 2.4 mmol), sodium carbonate (4.24 g, 40 mmol), toluene (80 mL), ethanol (20 mL) and water (20 mL) was placed in a 250 mL round-bottom flask, placed under vacuum and then backfilled with Ar(g) six times. Then tetrakis(triphenylphosphine)palladium(0) (120 mg, 0.10 mmol) was added and the resulting mixture was placed under vacuum and then backfilled with Ar(g) six times. The mixture was held in an oil bath at 50° C. for 48 h under argon protection. After cooling to room temperature, 100 mL of ethyl acetate and 100 mL of water were added and the layers were separated. The aqueous phase was extracted with ethyl acetate (3×50 mL), and the combined organic phases were washed with brine (2×100 mL), dried over MgSO$_4$, filtered, and evaporated in vacuo. The residue was purified by column chromatography over silica using ethyl acetate: petroleum ether (1:19) as eluent to afford the product as a light white solid (690 mg, 78%). mp 102-103° C. Elemental analysis (%) calcd for $C_{26}H_{24}BrF_3$ C, 68.03, H, 5.25; Found: C, 67.83, H, 5.30. $\lambda_{max}$(dichloromethane)/nm: 285 sh (log ε/dm$^3$ mol$^{-1}$ cm$^{-1}$ 4.45), 293 (4.50), 317 (4.49). $^1$H NMR (δ, 400 MHz, CDCl$_3$): 7.72 (1H, m), 7.58 (1H, d, J=8), 7.44-7.50 (5H, m), 6.91-7.01 (2H, m), 1.90-2.02 (4H, m), 0.67-0.74 (10H, m). $^{13}$C NMR (δ, 100 MHz, CDCl$_3$): 163.5, 163.4, 161.1, 161.0, 160.9(4), 160.9(2), 158.6, 158.5, 153.3, 150.6, 139.5(85), 139.5(76), 134.1, 131.5(2), 131.4(7), 131.4(3), 131.3(8), 130.0, 127.8(5), 127.8(3), 126.2, 125.7 (1), 125.6(7), 125.5(8), 125.5(4), 123.4(8), 123.4(5), 121.2 (5), 121.1(6), 119.8, 111.6(6), 111.6(2), 111.4(5), 111.4(1), 104.6(7), 104.4(2), 104.4(0), 104.1(5), 55.7, 42.5, 17.2, 14.4. MS (APCI): m/z found: 445.1 ([M-F+Na]$^+$).

Synthesis of SQF07114

2-(7-(2,4-difluorophenyl)-9,9-di-n-propyl-9H-fluoren-2-yl)-4,4,5,5-tetramethyl-1,3,2-dioxaborolane A mixture of 2-bromo-7-(2,4-difluorophenyl)-9,9-di-n-propyl-9H-fluorene (590 mg, 1.34 mmol), bis(pinacolato) diboron (508 mg, 2.0 mmol), potassium acetate (393 mg, 4.0 mmol), [1,1-bis(diphenylphosphino)ferrocene]palladium(II) dichloride dichloromethane complex (30 mg, 0.04 mmol) and 1,4-dioxane (20 mL) was heated under argon in an oil bath held at 105° C. for 16 h. The mixture was allowed to cool to room temperature and then the solvent removed under reduced pressure. Water (50 mL) and dichloromethane (50 mL) was added to the reaction and the organic phase was separated. The aqueous layer was extracted with dichloromethane (3×50 mL). The dichloromethane extracts were combined, washed with brine (2×50 mL), dried over anhydrous sodium sulfate, and filtered. The filtrate was collected and the solvent removed. The residue was purified by column chromatography over silica using dichloromethane: petroleum ether (1:3) as eluent to give a white solid (365 mg, 56%). mp 142-143° C.; mp (DSC)=120° C. (DSC scan rate 50° C./min); mp (TGA)=142° C. (TGA scan rate 50° C./min); $T_{5\% \ decomp}$=284° C. (sublimed); Tg=56° C. (DSC scan rate 100° C./min); Elemental analysis (%) cal. for $C_{31}H_{35}BF_2O_2$ C, 76.23; H, 7.22. Found: C, 76.21; H, 7.28. $\lambda_{max}$(dichloromethane)/nm: 286 sh (log ε/dm$^3$ mol$^{-1}$ cm$^{-1}$ 4.21), 295 (4.29), 319 (4.33). $\lambda_{max}$(em) (dichloromethane)/nm: 339, 353, 370 sh, 387 sh. $^1$H NMR (400 MHz, CDCl$_3$) δ 7.84 (1H, d, J=7.5), 7.78-7.79 (2H, m), 7.73 (1H, d, J=7.5), 7.45-7.51 (3H, m), 6.91-7.01 (2H, m), 1.95-2.06 (4H, m), 1.40 (12H, s), 0.66-0.73 (10H, m). $^{13}$C NMR (δ, 100 MHz, CDCl$_3$): 163.5, 163.3, 161.1, 160.9(8), 160.9(6), 161.8(6), 158.6, 158.5, 151.6, 150.2, 143.5, 140.5, 134.1, 133.8, 131.5(6), 131.5(1), 131.4(7), 131.4(2), 128.9, 127.6(2), 127.6(0), 125.8(9), 125.8(5), 125.7(6), 125.7(2), 123.5(2), 123.4(9), 120.1, 119.1, 111.6(1), 111.5(7), 111.4(0), 111.3 (6), 104.6(3), 104.3(8), 104.3(6), 104.1(1), 83.7, 55.4, 42.5, 24.9, 17.2, 14.4. m/z [ESI$^+$]: 489.1 ([M+H]+).

[6]: Synthesis of Polymer SQF0816
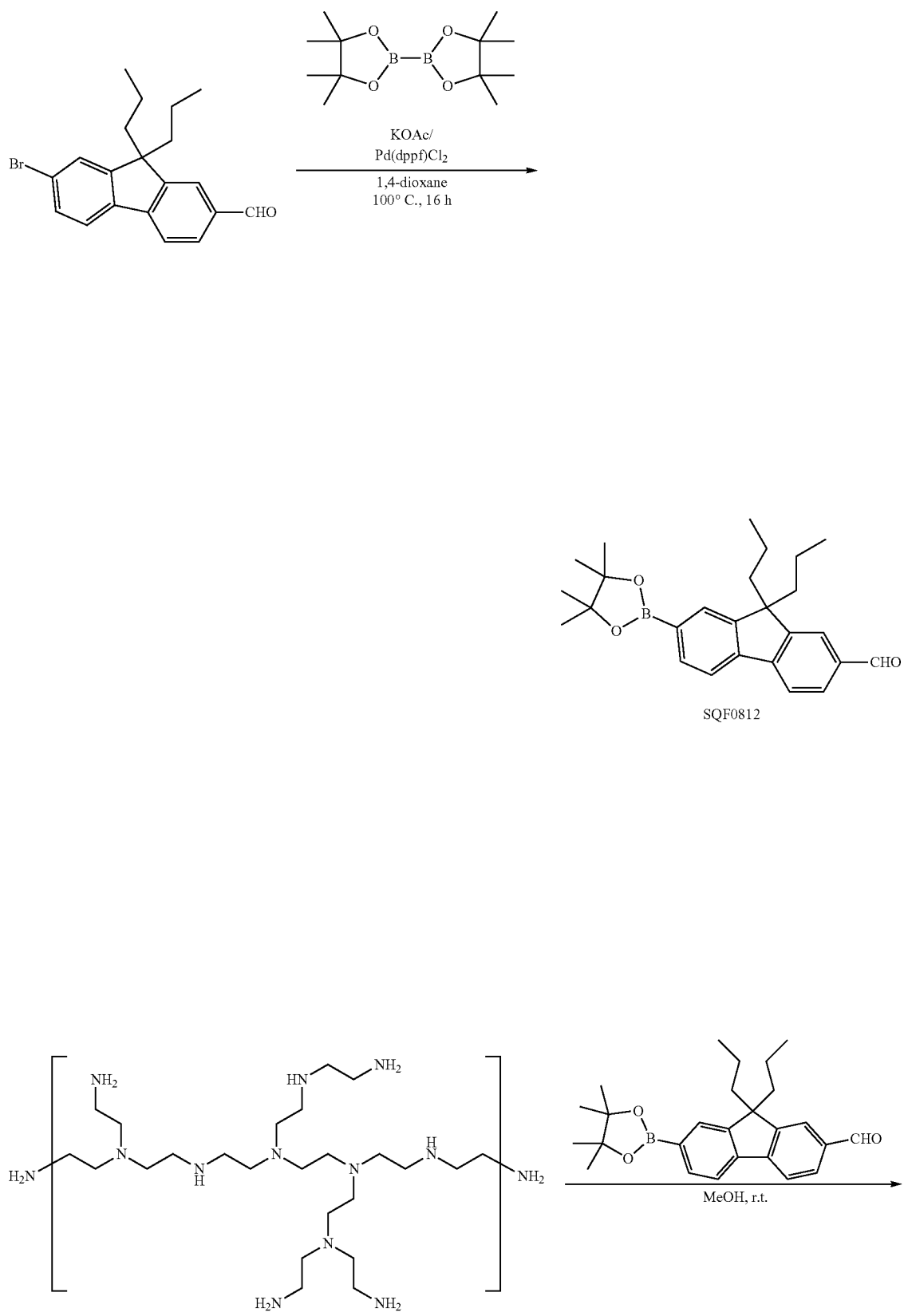

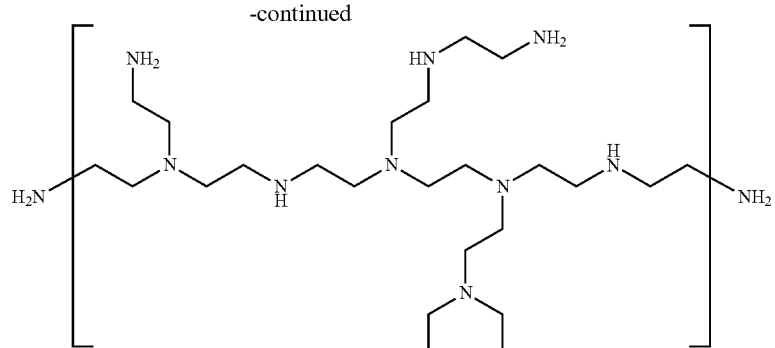

SQF0816

Synthesis of SQF0812

9,9-di-n-propyl-7-(4,4,5,5-tetramethyl-1,3,2-dioxaborolan-2-yl)-9H-fluorene-2-carbaldehyde A mixture of 7-bromo-9,9-di-n-propyl-9H-fluorene-2-carbaldehyde (1.33 g, 3.72 mmol), bis(pinacolato)diboron (1.13 g, 4.46 mmol), potassium acetate (1.10 g, 11.16 mmol), [1,1-bis(diphenylphosphino)ferrocene]palladium(II) dichloride dichloromethane complex (82 mg, 0.11 mmol) and 1,4-dioxane (20 mL) was heated under argon in an oil bath held at 100° C. for 16 h. The mixture was allowed to cool to room temperature and then the solvent removed under reduced pressure. Water (50 mL) and dichloromethane (50 mL) was added to the reaction and the organic phase was separated. The aqueous layer was extracted with dichloromethane (3×50 mL). The dichloromethane extracts were combined, washed with brine (2×100 mL), dried over anhydrous sodium sulfate, and filtered. The filtrate was collected and the solvent removed. The residue was purified by column chromatography over silica using ethyl acetate: petroleum ether (1:5) as eluent to give a white solid (1.258 g, 84%); mp 74-76° C. Elemental analysis (%) cal. for $C_{26}H_{33}BO_3$: C, 77.23; H, 8.23. Found: C, 77.12; H, 8.46. $^1$H NMR (400 MHz, $CDCl_3$) δ 10.06 (1H, s), 7.89 (1H, m), 7.83-7.85 (3H, m), 7.79 (1H, m), 7.62 (1H, dd, J=7 & 1.5), 7.77 (1H, d, J=7.5), 2.01-2.05 (4H, m), 1.39 (12H, s), 0.54-0.67 (10H, m). $^{13}$C NMR (100 MHz, $CDCl_3$) δ 192.4, 152.1, 151.2, 147.3, 142.3, 135.6, 133.9, 130.4, 129.0, 123.1, 120.4, 120.2, 83.9, 55.5, 42.3, 24.9, 17.1, 14.3.

Synthesis of SQF0816

A mixture of 9,9-di-n-propyl-7-(4,4,5,5-tetramethyl-1,3,2-dioxaborolan-2-yl)-9H-fluorene-2-carbaldehyde (10 mg, 0.025 mmol), polyethylenimine (branched, Mw=25,000 by LC, Mn=10,000 by GPC, Aldrich) (84 mg, 0.5 mmol —$NH_2$) and 1 mL of methanol was stirred at room temperature for 30 min. Then solvent was removed in vacuo to give a colorless sticky semi-solid.

Example 1a: Compound Preparation—Synthesis of Comparative Compound SQF1044

Scheme 7. Synthesis of SQF1044

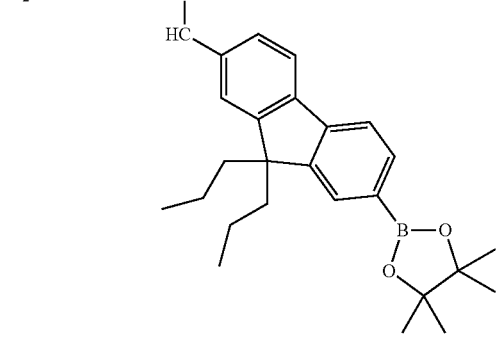

i. THF, Ar, -78° C., then n-BuLi, -78° C., 30 min
ii. 2-iso-propoxy-4,4,5,5-tetramethyl-1,3,2-dioxaborolane, -78° C., 30 min
iii. RT, 3 h

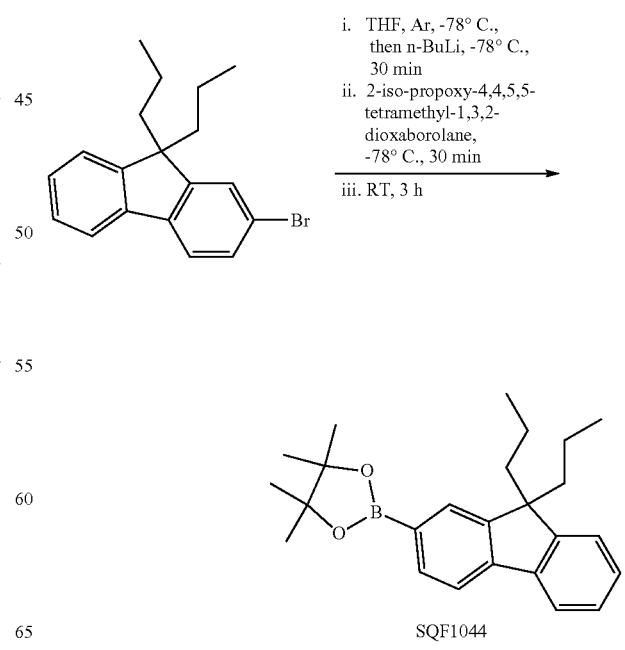

SQF1044

Synthesis of SQF1044

2-(9,9-Di-n-propyl-9H-fluoren-2-yl)-4,4,5,5-tetramethyl-1,3,2-dioxaborolane (SQF1044)

2-Bromo-9,9-di-n-propylfluorene (2.47 g, 7.5 mmol) was dissolved in anhydrous tetrahydrofuran (50 mL) under argon and the resulting solution was cooled to −78° C. in a dry ice/acetone bath. A solution of n-butyl lithium in hexane (2.5 M, 3.6 mL, 9.0 mmol) was added dropwise over 10 min and the mixture was stirred at −78° C. for another 30 min. 2-Iso-propoxy-4,4,5,5-tetramethyl-1,3,2-dioxaborolane (2.6 mL, 11.3 mmol) was added and the mixture was stirred at −78° C. for 30 min. Then the mixture was allowed to warm to room temperature and was stirred for 3 h at room temperature. The mixture was quenched with water (50 mL) and extracted with ethyl acetate (3×50 mL). The combined organic layers were washed with brine (100 mL), dried over anhydrous sodium sulphate and filtered. The filtrate was collected and the solvent removed. The residue was purified by column chromatography over silica using dichloromethane:petroleum ether (1:10-1:3) as eluent to give SQF 1044 as a white solid (1.28 g, 45%). mp 74-75° C. Elemental analysis (%) calcd for $C_{25}H_{33}BO_2$ C, 79.8, H, 8.8; Found: C, 80.0, H, 8.8. $\lambda_{max}$(dichloromethane)/nm: 273 (log ε/dm$^3$ mol$^{-1}$ cm$^{-1}$ 4.46), 280 sh (4.48), 283 (4.51), 298 (4.30), 303 sh (4.23), 310 (4.43). $\lambda_{max}$(fluorescence) (dichloromethane)/nm: 312, 326, 340 sh. $^1$H NMR (500 MHz, CDCl$_3$) δ 7.81 (1H, ddd, J=1, J=1, J=7.5, Fl-H), 7.76 (1H, d, J=1, Fl-H), 7.71-7.73 (1H, m, Fl-H), 7.70 (1H, ddd, J=1, J=1, J=7.5, Fl-H), 7.34-7.37 (1H, m, Fl-H), 7.30-7.33 (2H, m, Fl-H), 1.92-2.04 (4H, m, Pr—H), 0.57-0.65 (10H, m, Pr—H). $^{13}$C NMR (125 MHz, CDCl$_3$) 151.3, 149.8, 144.1, 140.9, 133.7, 128.8, 127.5, 126.7, 122.9, 120.1, 118.9, 83.7, 55.3, 42.6, 24.9, 17.1, 14.4. m/z [ESI$^+$]: 377.1 ([M+H]$^+$).

Example 1b: Compound Preparation—Synthesis of Organic Peroxides

Organic peroxides were prepared using published methods, for example in accordance with the route described in P. Goodman, University of Nebraska-Lincoln, *The Electrochemical Analysis of Bovine Bone Derived Supercapacitors, Organic Peroxide Explosives, and Conducting Polymer Nanojunctions*, 2013, p 67.
Synthesis of Triacetone Triperoxide (TATP)
A mixture of acetone (1.1 g, 1.4 mL, 19 mmol) and hydrogen peroxide (30%, 2.3 g, 2.1 mL, 19 mmol) in a 10-mL RBF was cooled to 0° C. and then 2 drops of concentrated HCl (37%) was added. The mixture was stirred at room temperature for 16 h. The product, which was a white solid, was collected via vacuum filtration and washed thoroughly with 500 mL of deionized water (note: a large volume of water is necessary to remove residual $H_2O_2$). The TATP was dried by allowing the solid to remain in the vacuum filter with flowing air for approximately 30 min before collection. The dried TATP (302 mg) was placed in a 25 mL glass jar, sealed and stored in a fridge.

Example 2: Coating of the Optical Sensing Element

The coating of the optical sensing elements on planar glass and quartz substrates was achieved by drop casting from solution. The typical solution comprises of 2 mg of sensing compound, up to 20 mg of base, either tetra(n-butylammonium)hydroxide (n-Bu$_4$NOH) or polyethylenimine (PEI) or both, and optionally up to 10 mg of polymer (PEI or PEO), and 0.20-0.50 mL of spectrophotometric ethanol. The solutions were stirred at room temperature (or slightly warming to 40° C.) in a 1 mL-vial for 10 min before use. The coatings were fabricated by drop casting on the substrate at a loading amount of 5-25 μL/cm$^2$ and then dried under nitrogen stream and/or vacuum.

Coatings inside a capillary were prepared by immersing one end of the capillary into the solution. Once the capillary was filled the excess solution was wicked out with a paper towel and the residue dried with a nitrogen stream and/or vacuum.

Example 3: TATP Vapour Generation and Acid-Assisted Decomposition

Vapour generation: 200 mg of TATP powder (prepared according to the method of Example 1b) was mixed with 10.5 g of sand and then filled into a glass tube (Φ0.5 cm×20 cm). The glass tube was connected to a gas mass flow controller (MFC) at one end and to a Teflon tube (Φ2 mm×20 mm) filled with Amberlyst-15 solid-state acid at the other end. The Amberlyst-15 was the catalyst used to decompose TATP into hydrogen peroxide. A second gas MFC was employed for dilution. Nitrogen was used as both the carrier gas and dilution gas. The PL response without hydrogen peroxide input was tested in air, rather than in nitrogen gas, in order to predict the LODs in practice.

Example 3a: TATP Decomposition Study

The decomposition products of the TATP vapour were generated using the procedure described in Example 3. The product was collected by bubbling the vapour through 1 mL of DMSO-d6 at a flow rate of 30 mL/min for 1 h prior to acquiring the $^1$H NMR spectrum. With reference to FIG. 6, the chemical shift (δ) of TATP was 1.36 ppm (bottom spectrum). In the top spectrum, acetone (a decomposition product) can be observed at δ=2.08 ppm. The TATP peak in the top spectrum was less than 0.5% of the integrated intensity of the acetone peak. This demonstrates that TATP can be fully decomposed using a short tube with Amberlyst-15.

Figure 1A:
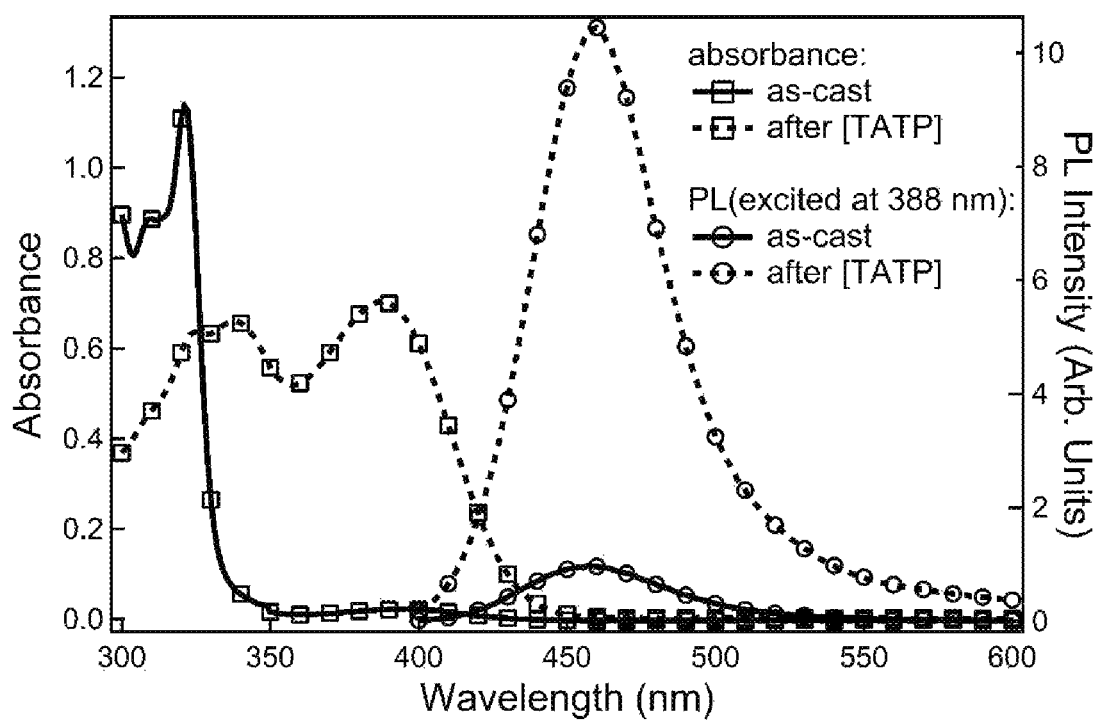
Figure 1B:
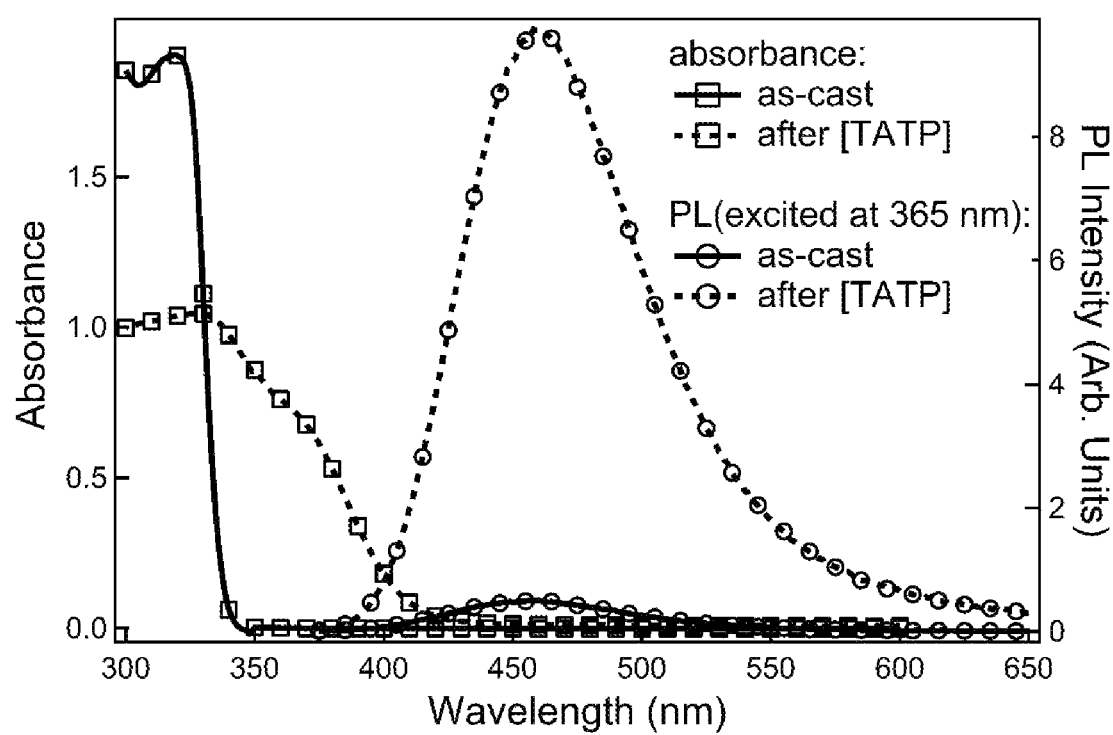
Figure 1C:
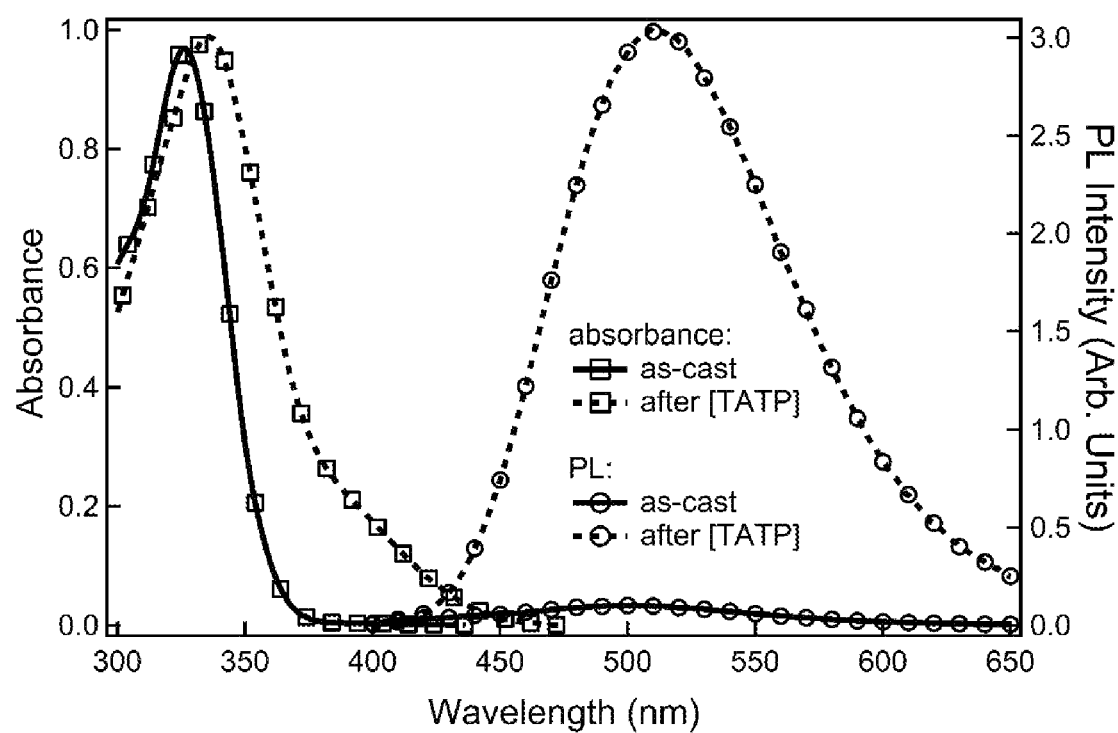

Example 4: Photophysical Changes Before and After Exposing to Peroxide Vapour As shown in FIGS. 1*a*-1*c*, the optical sensing elements comprising the sensing compound and base show new absorption peaks/shoulders at longer wavelength after exposure to hydrogen peroxide following TATP decomposition. Excitation at the predetermined wavelength within these new absorption peaks/shoulders of the reporter compound gives PL peaks in the range of 454-517 nm. The PL peak wavelength is significantly influenced by the type of electron-withdrawing moiety. Stronger electron-withdrawing moiety is found to give a PL peak at longer wavelength.

Figure 1D:
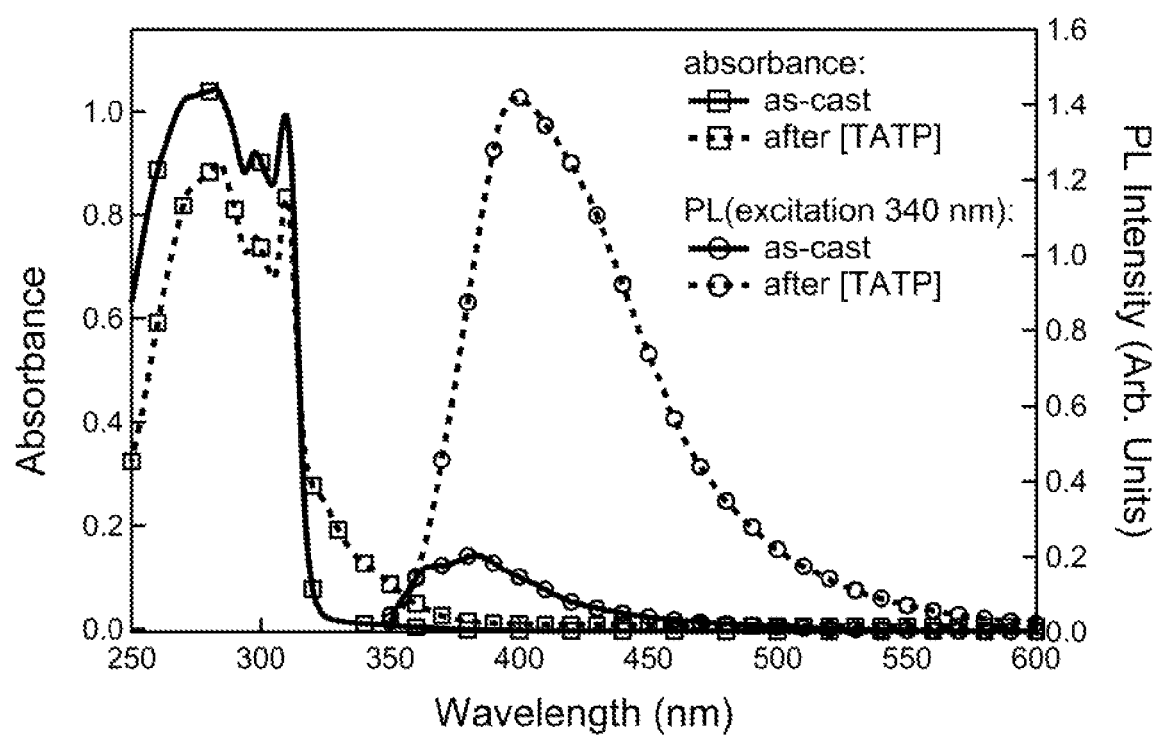

By way of comparison, the structure of the fluorenyl boronate compound SQF1044 does not include an electron withdrawing group. As shown in FIG. 1*d*, an optical sensing element comprising SQF1044 and base does show a new absorption shoulder at longer wavelength (approximately 340 nm) after exposure to hydrogen peroxide following TATP decomposition. However, it can be clearly seen from FIG. 1*d* that this new absorption is less significant when compared to that observed for the sensing compounds of the invention comprising an electron-withdrawing group (Ar2).

Similarly, the PL peak wavelength is not as shifted to longer wavelengths when there is no electron withdrawing group.

Table 1 illustrates the importance of the choice of predetermined excitation wavelength and how it can be used to specifically excite the reporter compound.

TABLE 1

Comparison of films of sensing compound (boronate ester) and reporter compound (phenolate)

| Sensing compound | Wave-length/nm | Sensing compound | | Reporter compound | |
|---|---|---|---|---|---|
| | | Absorbance (Yes/No?) | Photoluminescence (Yes/No?) | Absorbance (Yes/No?) | Photoluminescence (Yes/No?) |
| SQF0724 | 321 | Y | Y | Y | Y |
| | 388 | N | N | Y | Y |
| SQF07114 | 319 | Y | Y | Y | Y |
| | 360 | N | N | Y | Y |
| SQF0784 | 326 | Y | Y | Y | Y |
| | 388 | N | N | Y | Y |
| SQF0782 | 329 | Y | Y | Y | Y |
| | 359 | N | N | Y | Y |

Figure 3A:
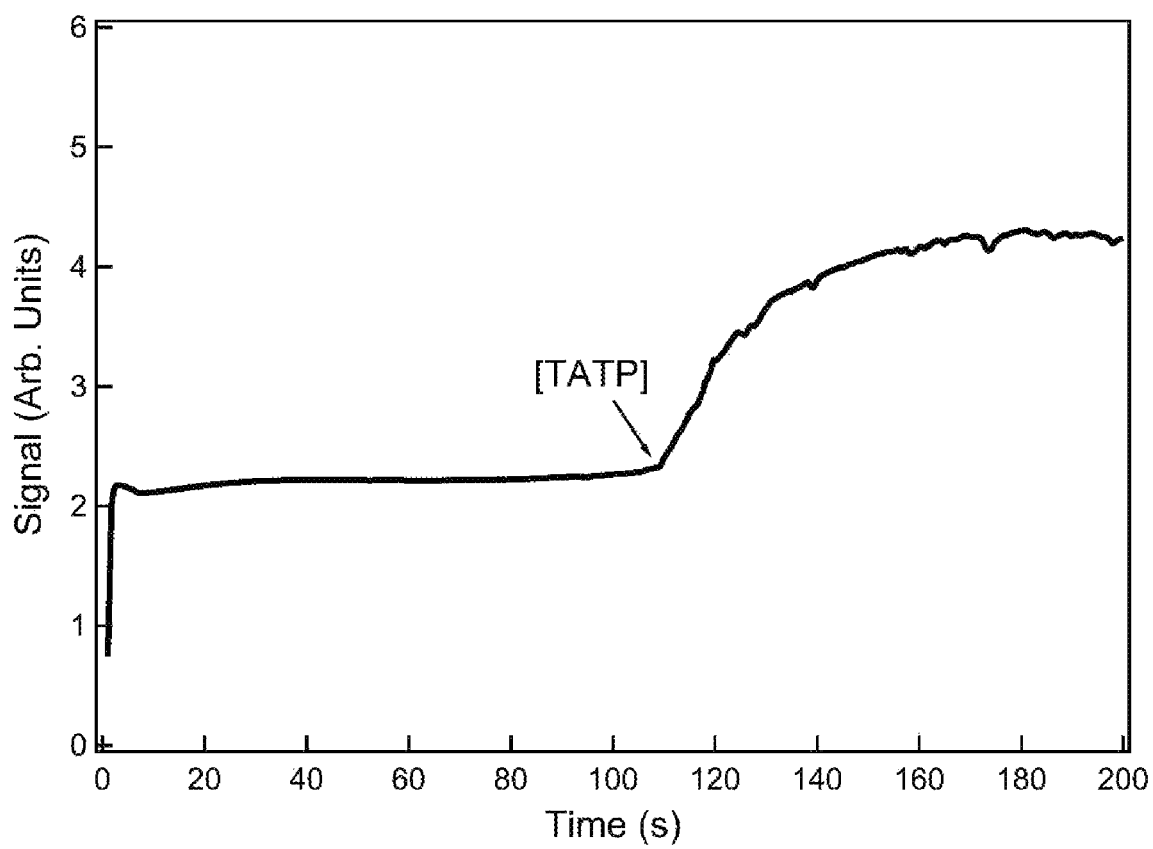
FIG. 3a is a graph showing the PL response of capillary coated internally with a film comprising SQF0724 versus time. Base: n-Bu$_4$NOH (6 eq). [TATP] represents the conditioned sample from TATP generated using Amberlyst-15 as catalyst.
Figure 3B:
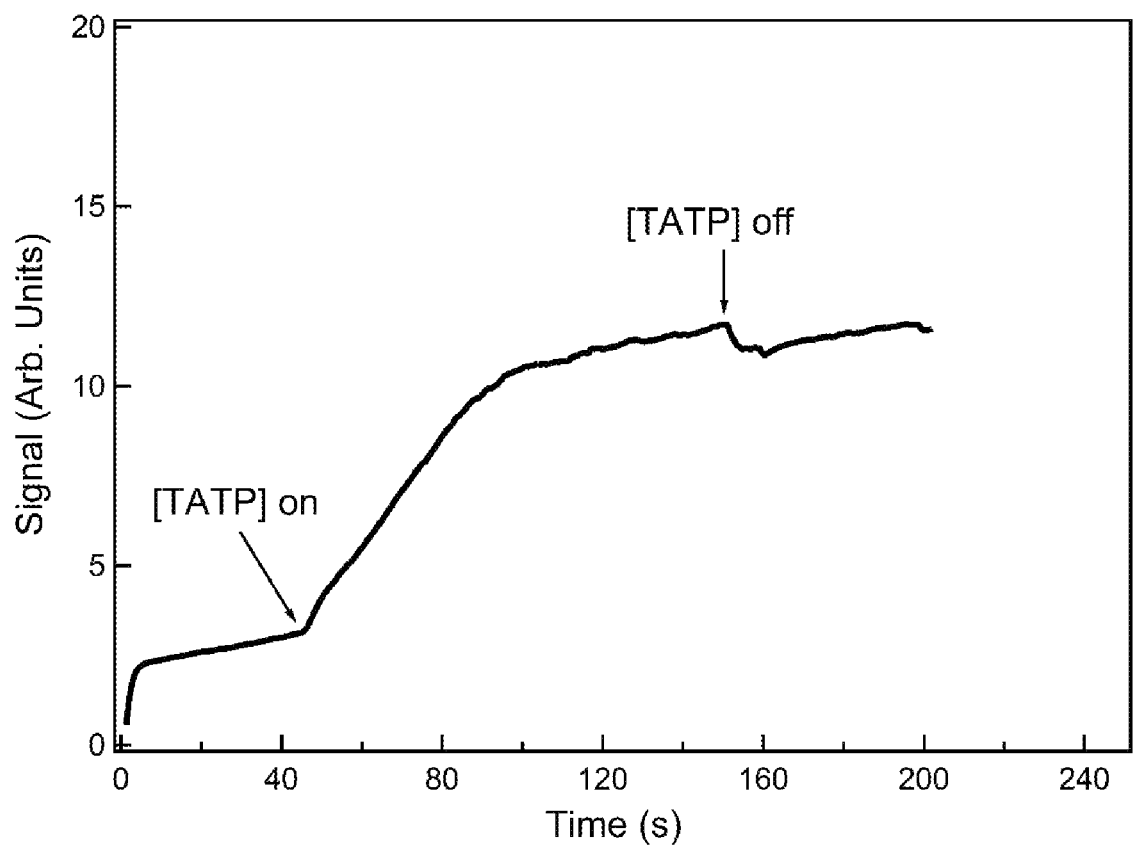
FIG. 3b is a graph showing the PL response of capillary coated internally with a film comprising SQF0816 versus time. Base: PEI and n-Bu$_4$NOH (mass ratio: 4/1). [TATP] represents the conditioned sample from TATP generated using Amberlyst-15 as catalyst.
Figure 3C:
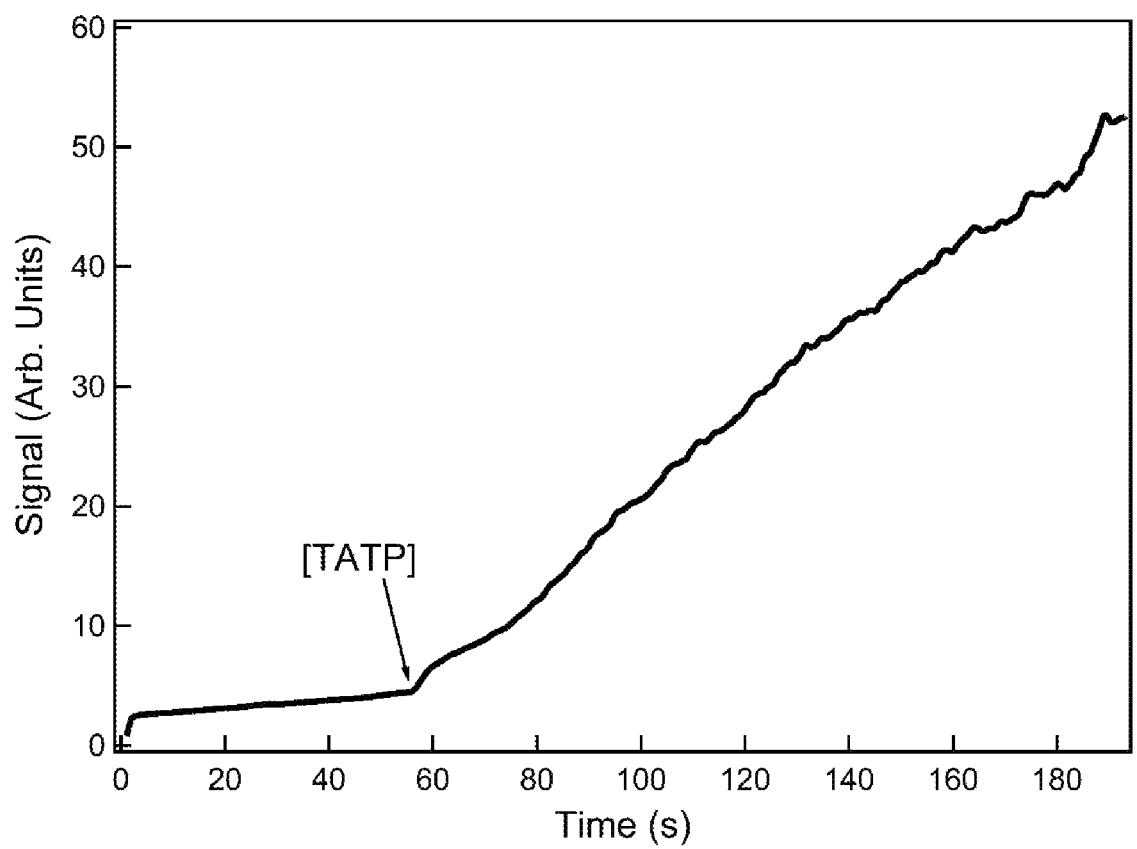
FIG. 3c is a graph showing the PL response of capillary coated internally with a film comprising SQF07114 versus time. Base: PEI (mass ratio: SQF07114/PEI=1/8). [TATP] represents the conditioned sample from TATP generated using Amberlyst-15 as catalyst.

FIGS. 3a,c,d illustrate the photoluminescence response from films comprising SQF0724 or SQF07114 coated on the inside of a capillary and excited with the output from an LED with peak emission at 395 nm. The predetermined wavelength was selected to specifically excite the reporter compound as shown in the data from Table 1. The advantage is the elimination of any signal from unreacted sensor compound and maximizing the signal to noise.

Example 5: Interferents

Figure 2:
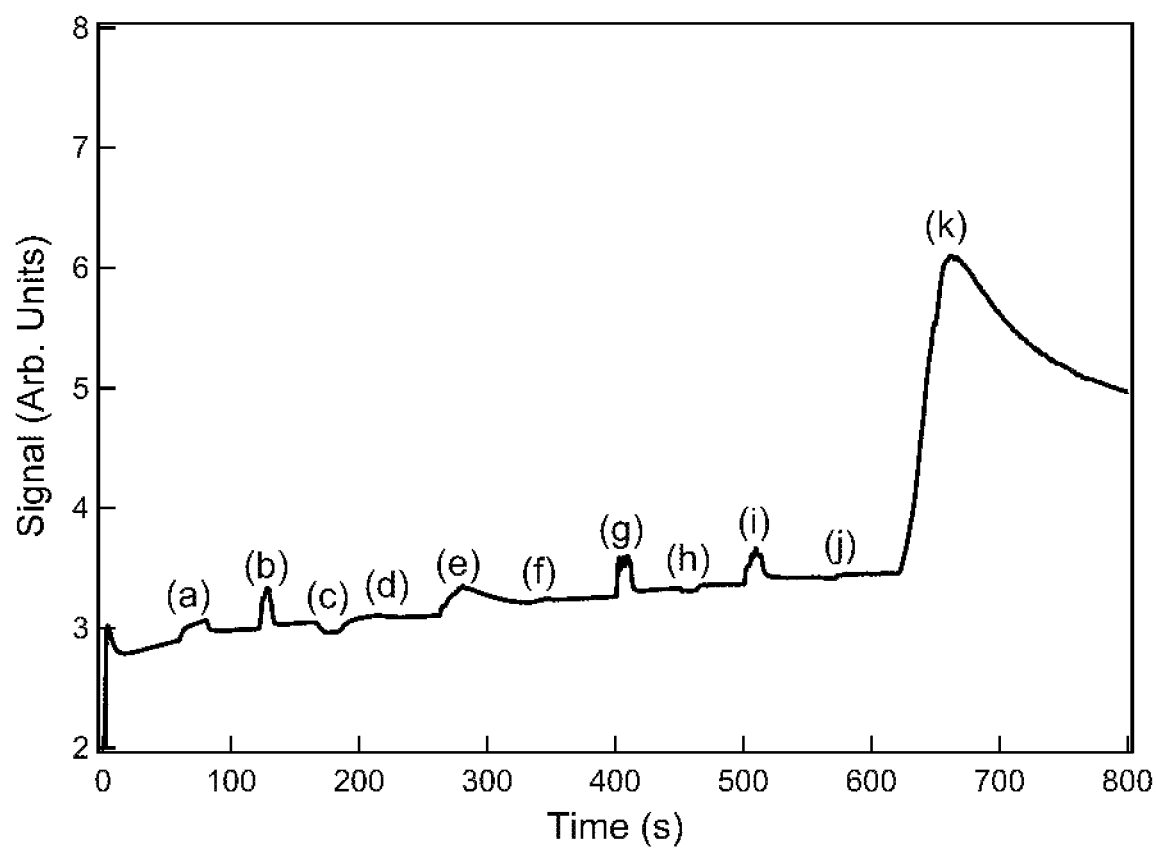

Compared with some common interferents such as ethanol, perfume and sunscreen, hydrogen peroxide from TATP decomposition gives significantly higher signals. Most importantly, the signal from hydrogen peroxide is irreversible while that from interferents are reversible, which can be used to identify the presence of hydrogen peroxide. The photoluminescence response of a capillary coated internally with a film comprising SQF0724 as it comes into contact with a series of vapour interferents is shown in FIG. 2. Each interferent, which are labelled (a) to (j) gives a small and reversible change in the photoluminescence signal. In contrast, the response to a conditioned sample of TATP vapour (k) results in a much greater and longer-lasting photoluminescence change.

The invention claimed is:

1. An optical sensing element for vapour phase detection of hydrogen peroxide, the optical sensing element comprising a sensing compound provided as a coating on a substrate, wherein the sensing compound is a compound that on exposure to hydrogen peroxide forms a luminescent reporter compound when excited with stimulating radiation at a predetermined wavelength that the sensing compound does not absorb, and wherein the sensing compound is a compound of general formula:

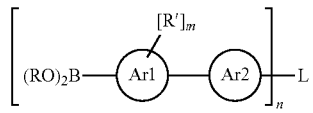

in which:

each R group can be the same or different $C_{2-5}$ alkyl moiety or together with the oxygen atoms to which they are attached form a cyclic structure containing up to 5 carbon atoms, optionally substituted by one or more $C_{1-4}$ alkyl groups;

Ar1 is a (hetero)aromatic moiety and/or comprises fused (hetero)aromatic rings or a chain of (hetero)aromatic or fused (hetero)aromatic rings moieties;

Ar2 is an aromatic unit with electron withdrawing groups attached or a higher electron affinity heteroaromatic moiety selected from an imidazole, pyrazine, triazole, benzotriazole, thiadiazolebenzotriazole, oxadiazole, oxazole, thiazole, thiadiazole, benzothiadiazole, benzobis(thiadiazole), quinoxaline, and thiodiazoloquinoxaline;

R' is a solubilising group selected from straight or branched chain alkyl groups containing up to 10 carbon atoms, ethylene glycol chains including 2-methoxymethyl, 2-methoxyethyl, 2-(2-methoxyethoxy)ethyl, and 2-(2-(2-methoxyethoxy)ethoxy)ethyl, and dendrons that include one or more aryl rings and/or hetero atoms;

m is an integer equal to 1 or greater;

n is an integer equal to 1 or greater;

L is a linker unit that is present when n is greater than 1, wherein L is a polymer, carbon atom or alkyl group; and/or wherein the sensing compound is selected from the following compounds

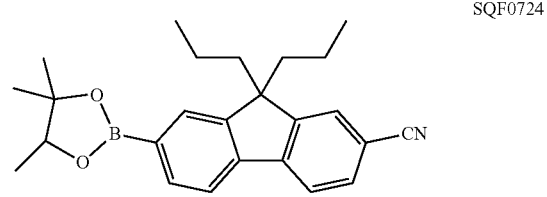
SQF0724

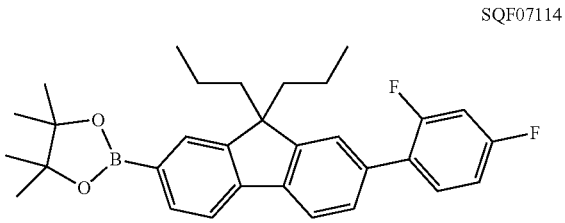
SQF07114

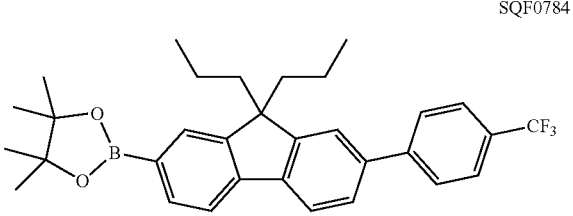
SQF0784

39
-continued

SQF0756

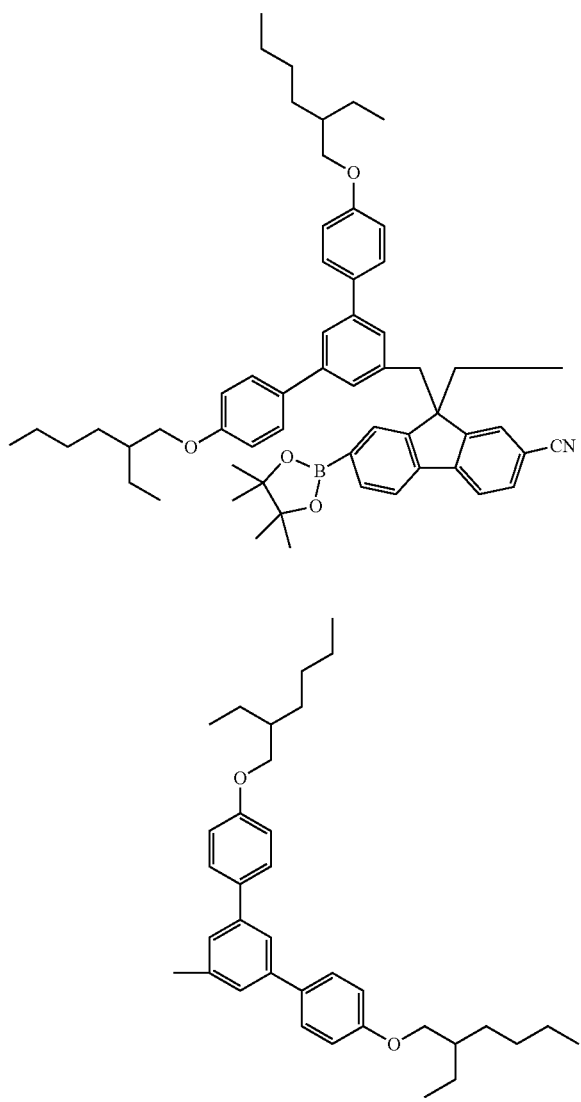

SQF0816

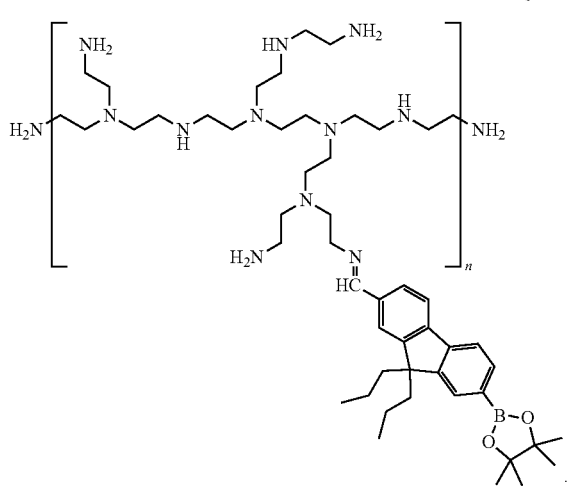

40
-continued

SQF0782

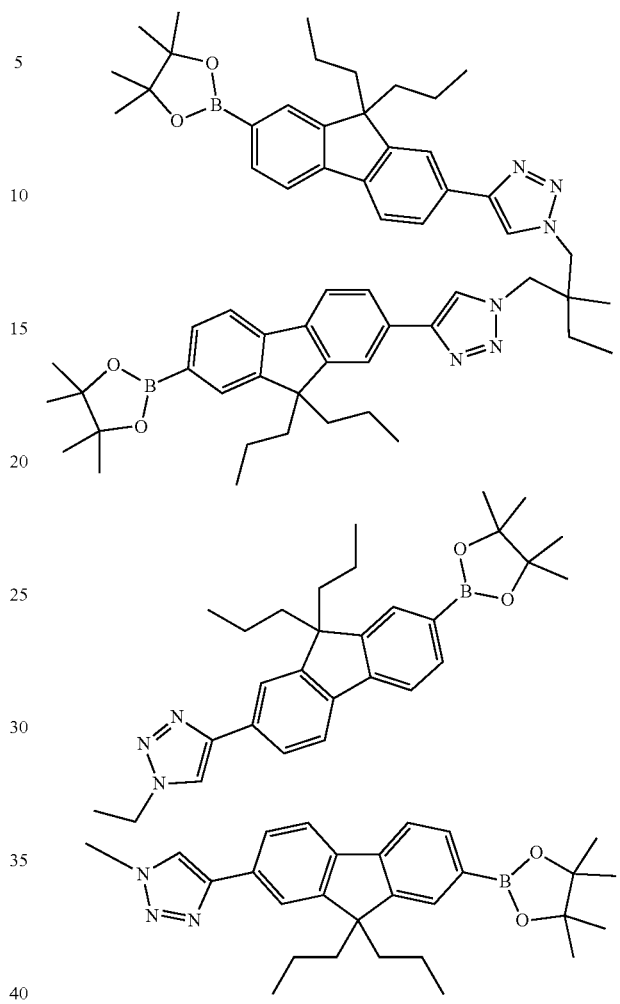

2. The optical sensing element of claim 1, wherein the sensing compound is a 2-fluorenyl boronic acid pinacol ester.

3. A sensing device for vapour phase detection of hydrogen peroxide in a sample, the sensing device comprising:
an optical sensing element as claimed in claim 1;
an irradiation source for irradiating the optical sensing element with stimulating radiation at the predetermined wavelength;
a detector for measuring luminescence of the optical sensing element; and
means for delivering the sample for contacting with the optical sensing element.

4. A sensing device for detecting organic peroxide in a sample, the sensing device comprising:
means for decomposing organic peroxide in the sample to hydrogen peroxide to produce a conditioned sample;
an optical sensing element as claimed in claim 1;
an irradiation source for irradiating the optical sensing element with stimulating radiation at the predetermined wavelength;
a detector for measuring luminescence of the optical sensing element; and
means for delivering the conditioned sample for contacting with the optical sensing element.

5. A device according to claim 4, wherein the means for decomposing organic peroxide in the sample to hydrogen peroxide comprises a solid-state acidic catalyst.

6. A method for vapor phase detection of hydrogen peroxide in a sample, which method comprises the steps: (a) irradiating an optical sensing element as claimed in claim 1 at the predetermined wavelength; (b) contacting the sample with the optical sensing element; (c) measuring luminescence of the optical sensing element after contacting with the sample; and (d) determining whether hydrogen peroxide is present in the sample based on the measurement obtained in step (c).

7. A method of detecting an organic peroxide in a sample, the method comprising the steps: (a) processing the sample to cause organic peroxide in the sample to decompose to yield vapour of hydrogen peroxide to produce a conditioned sample; (b) irradiating an optical sensing element as claimed in claim 1 at the predetermined wavelength; (c) contacting the conditioned sample with the optical sensing element; (d) measuring luminescence of the optical sensing element after contacting with the conditioned sample; (e) determining whether hydrogen peroxide is present in the conditioned sample based on the measurement obtained in (d); and (f) using a determination that hydrogen peroxide is present in step (e) as indication that the organic peroxide is present in the sample.

8. The optical sensing element of claim 1, wherein the solubilizing group of straight or branched chain alkyl groups containing up to 10 carbon atoms include n-propyl groups.

9. The optical sensing element of claim 1, wherein the dendrons include phenyl.

* * * * *